United States Patent
Rathi et al.

(10) Patent No.: US 12,194,169 B2
(45) Date of Patent: Jan. 14, 2025

(54) METHODS AND APPARATUS FOR SANITIZING AN AUTONOMOUS VEHICLE

(71) Applicant: Nuro, Inc., Mountain View, CA (US)

(72) Inventors: Benjamin Bhanu Rathi, Novi, MI (US); Kun Geng, Fremont, CA (US); Peter Jon Kardassakis, Mountain View, CA (US); Steven Yewen Wu, San Mateo, CA (US); Robert Jong Kon Kim, Palo Alto, CA (US)

(73) Assignee: NURO, INC., Mountain View, CA (US)

( * ) Notice: Subject to any disclaimer, the term of this patent is extended or adjusted under 35 U.S.C. 154(b) by 374 days.

(21) Appl. No.: 17/201,327

(22) Filed: Mar. 15, 2021

(65) Prior Publication Data
US 2021/0308300 A1    Oct. 7, 2021

Related U.S. Application Data

(60) Provisional application No. 63/006,067, filed on Apr. 6, 2020.

(51) Int. Cl.
*A61L 2/10*    (2006.01)
*B08B 3/08*    (2006.01)
(Continued)

(52) U.S. Cl.
CPC ............... *A61L 2/10* (2013.01); *B08B 3/08* (2013.01); *B60S 1/64* (2013.01); *B60S 1/66* (2013.01);
(Continued)

(58) Field of Classification Search
CPC ..... B08B 3/08; B60S 1/64; A61L 2/04; A61L 2/16; A61L 2/10
See application file for complete search history.

(56) References Cited

U.S. PATENT DOCUMENTS

| | | | |
|---|---|---|---|
| 7,138,087 B1 * | 11/2006 | Malkin | A61L 2/07 422/26 |
| 2004/0251706 A1 * | 12/2004 | Kim | B60N 3/046 296/75 |

(Continued)

FOREIGN PATENT DOCUMENTS

| | | | |
|---|---|---|---|
| CN | 107651049 A | | 2/2018 |
| JP | 2008200422 A | * | 9/2008 |

OTHER PUBLICATIONS

International Preliminary Report on Patentability received Oct. 6, 2022 for PCT application PCT/US2021/02247.

*Primary Examiner* — Donald R Spamer
*Assistant Examiner* — Priscilla Browning
(74) *Attorney, Agent, or Firm* — Edell, Shapiro & Finnan, LLC

(57) ABSTRACT

According to one aspect, a vehicle includes a first compartment, a system, and a first sanitizing arrangement. The first compartment has a plurality of walls that define a space, and the system is configured to enable the vehicle to travel autonomously. The system includes a power system configured to provide power to the first compartment. The first sanitizing arrangement includes at least a first sanitizing component, the at least first sanitizing component being included in the first compartment, wherein the first sanitizing arrangement is configured to be activated to sanitize the plurality of walls and the space.

7 Claims, 21 Drawing Sheets

(51) Int. Cl.
*B60S 1/64* (2006.01)
*B60S 1/66* (2006.01)

(52) U.S. Cl.
CPC ........ *A61L 2202/11* (2013.01); *A61L 2202/17* (2013.01); *A61L 2202/25* (2013.01)

(56) References Cited

U.S. PATENT DOCUMENTS

| | | |
|---|---|---|
| 2008/0078514 A1 | 4/2008 | Weerawarna et al. |
| 2012/0223216 A1* | 9/2012 | Flaherty ............... G05D 1/0242 901/1 |
| 2013/0251590 A1* | 9/2013 | Golden .................. A01N 59/00 422/24 |
| 2015/0360663 A1* | 12/2015 | Svensson ................ B60T 8/172 701/70 |
| 2017/0049915 A1* | 2/2017 | Brais .................... H05B 47/115 |
| 2018/0080188 A1 | 3/2018 | Pickover et al. |
| 2019/0076558 A1* | 3/2019 | Zhang-Miske .......... B60Q 3/00 |
| 2019/0091738 A1 | 3/2019 | Chen |
| 2019/0358818 A1* | 11/2019 | Kanitz ..................... B60S 1/64 |
| 2019/0392295 A1 | 11/2019 | Kanitz |

* cited by examiner

*344a'*

*344a"*

METHODS AND APPARATUS FOR SANITIZING AN AUTONOMOUS VEHICLE

PRIORITY CLAIM

This patent application claims the benefit of priority under 35 U.S.C. § 119 to U.S. Provisional Patent Application No. 63/006,067, filed Apr. 6, 2020 and entitled "METHODS AND APPARATUS FOR UTILIZING AN AUTONOMOUS VEHICLE WHEN A SHELTER-IN-PLACE ORDER IS IN EFFECT," which is incorporated herein by reference in its entirety.

TECHNICAL FIELD

The disclosure relates to the use of autonomous vehicles. More particularly, the disclosure relates to providing cleaning capabilities for autonomous vehicles, and contents transported by the autonomous vehicles, when biological threats are present.

BACKGROUND

In some situations, it may not be practical, desirable, or possible for individuals to leave their homes to acquire necessary items or to obtain necessary services. For example, during a crisis such as a global pandemic, when shelter-in-place or stay-at-home orders are in effect, individuals may not be able to or be willing to leave their homes to procure goods and/or to receive services.

The ability to safely receive deliveries of necessary items may allow individuals to remain sheltered-in-place or at home. In general, during a pandemic, individuals may feel safer if they are able to remain sheltered-in-place, and avoid venturing to places where there may be a biological threat. By avoiding places where there may be a biological threat, e.g., virus transmission, an individual may protect himself or herself from succumbing to the biological threat, e.g., becoming infected with a virus.

BRIEF DESCRIPTION OF THE DRAWINGS

The disclosure will be readily understood by the following detailed description in conjunction with the accompanying drawings in which.

DESCRIPTION OF EXAMPLE EMBODIMENTS

General Overview

Figure 1:
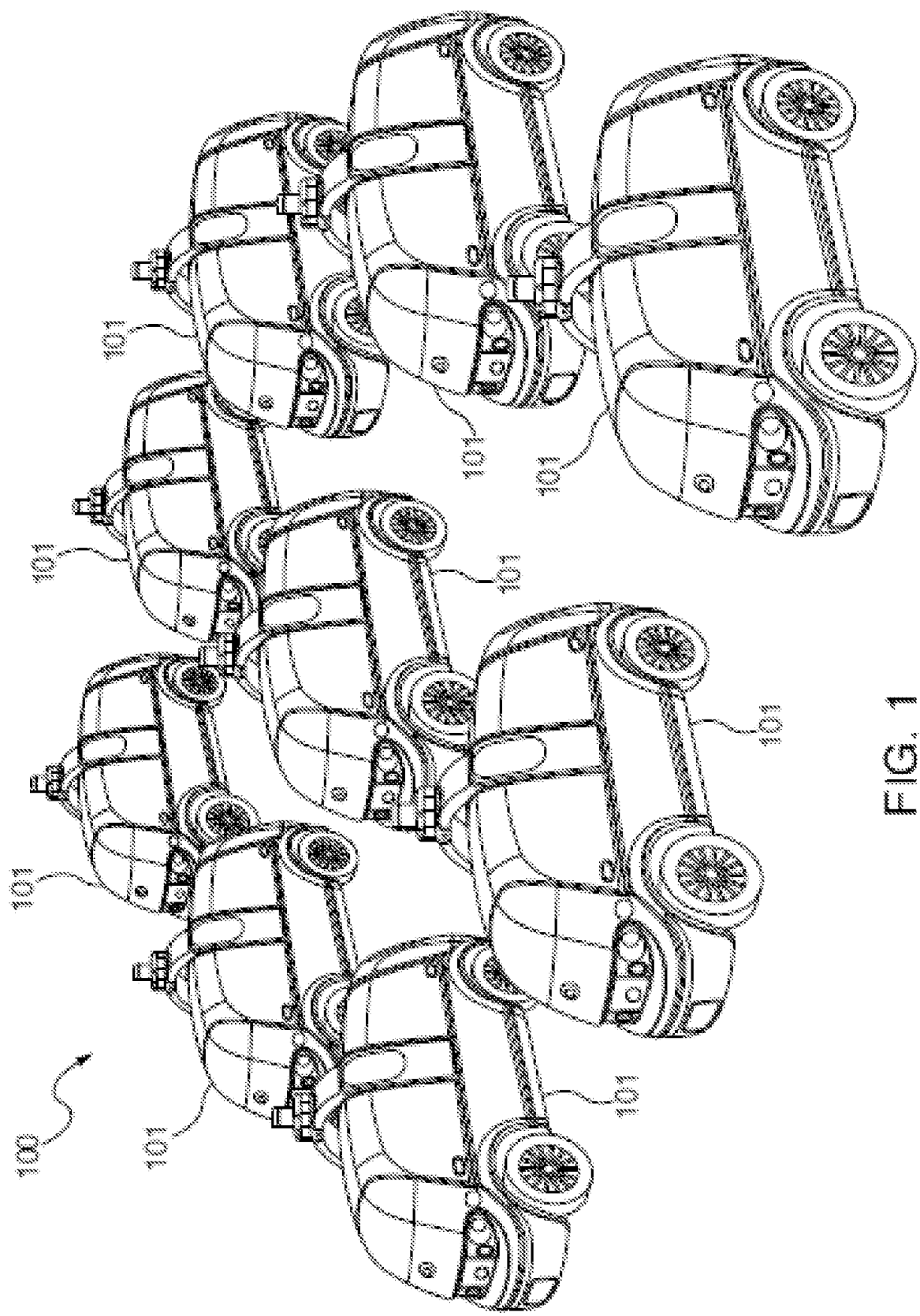
FIG. 1 is a diagrammatic representation of an autonomous vehicle fleet in accordance with an embodiment.

An autonomous delivery vehicle may be deployed to facilitate deliveries, e.g., when it is not advisable or impossible for individuals to leave their places of residence. A delivery vehicle may disinfect or otherwise clean items included in deliveries such that the deliveries may be safely received substantially without the recipient having to worry about disinfecting the items upon receipt. Such a delivery vehicle may also disinfect compartments arranged to contain items.

In accordance with one embodiment, a vehicle includes a first compartment, a system, and a first sanitizing arrangement. The first compartment has a plurality of walls that define a space, and the system is configured to enable the vehicle to travel autonomously. The system includes a power system configured to provide power to the first compartment. The first sanitizing arrangement includes at least a first sanitizing component, the at least first sanitizing component being included in the first compartment, wherein the first sanitizing arrangement is configured to be activated to sanitize the plurality of walls and the space.

According to another embodiment, a vehicle includes a first compartment that has a plurality of walls that define a space, and a first sanitizing arrangement. The plurality of walls includes a first wall and a second wall, the first compartment being arranged to carry an item in the space. The first sanitizing arrangement includes at least one ultraviolet (UV) light source, the at least one UV light source being coupled to the first wall and configured to generate a first UV light wave directed towards the second wall, the first sanitizing arrangement further including a logic arrangement configured to activate the at least one UV light source to provide UV sanitization.

According to yet another embodiment, a method comprises determining when a compartment onboard a vehicle is to be cleaned, the vehicle including at least a first cleaning arrangement, the first cleaning arrangement configured to implement a cleaning process to clean the compartment, wherein the first cleaning arrangement includes at least one UV light source. The method also includes determining at least one parameter for the cleaning process when it is determined that the compartment is to be cleaned, determining whether the vehicle is in condition to be cleaned when it is determined that the compartment is to be cleaned, and activating the first cleaning arrangement to initiate the cleaning process when it is determined that the vehicle is in condition to be cleaned. It is determined when the compartment is at a desired level of cleanliness after initiating the cleaning process. The cleaning process is continued when it is determined that the compartment is not at the desired level of cleanliness, and the cleaning process is completed when it is determined that the compartment is at the desired level of cleanliness.

DESCRIPTION

Situations may arise in which autonomous delivery vehicles may be leveraged to not only deliver goods, but to deliver the goods in a manner that effectively protects recipients of the delivered goods. For example, during a pandemic in which individuals are expected to shelter-in-place or to stay at home to avoid the spread of illness or disease, autonomous delivery vehicles may deliver goods to individuals at their homes in a way that enables the individuals to receive the goods without having to come into physical contact with other individuals, and with confidence that the goods are not contaminated. Avoiding physical contact with other individuals may allow for adherence to social distancing guidelines, for example, and, thus, slow the spread of illness or disease during a pandemic or otherwise. The spread of illness or disease may further be slowed when received goods are cleaned to remove or to deactivate contaminants such as viruses.

Providing mechanisms in an autonomous vehicle that allow for goods transported in the autonomous vehicle to be disinfected, sanitized, decontaminated, sterilized, and/or otherwise cleaned may give a customer confidence that the goods are "safe," e.g., not covered with a contaminant such as a virus. In one embodiment, upon arrival of an autonomous vehicle at a customer location, the customer may be allowed to retrieve goods from the autonomous vehicle in a contactless manner, or substantially without physically touching the autonomous vehicle. The ability to retrieve a good or item without physically touching the autonomous vehicle further allows the customer to be more confident that the overall delivery process is safe, and did not place him or her at a relatively high risk of being exposed to a contaminant.

Autonomous vehicles such as autonomous delivery vehicles may generally operate as part of an overall fleet of vehicles. Referring initially to FIG. 1, an autonomous vehicle fleet will be described in accordance with an embodiment. An autonomous vehicle fleet 100 includes a plurality of autonomous vehicles 101, or robot vehicles. Autonomous vehicles 101 are generally arranged to transport and/or to deliver cargo, items, and/or goods. Autonomous vehicles 101 may be fully autonomous and/or semi-autonomous vehicles. In general, each autonomous vehicle 101 may be a vehicle that is capable of travelling in a controlled manner for a period of time without intervention, e.g., without human intervention. As will be discussed in more detail below, each autonomous vehicle 101 may include a power system, a propulsion or conveyance system, a navigation module, a control system or controller, a communications system, a processor, and a sensor system.

Dispatching of autonomous vehicles 101 in autonomous vehicle fleet 100 may be coordinated by a fleet management module (not shown). The fleet management module may dispatch autonomous vehicles 101 for purposes of transporting, delivering, and/or retrieving goods or services in an unstructured open environment or a closed environment.

Figure 2:
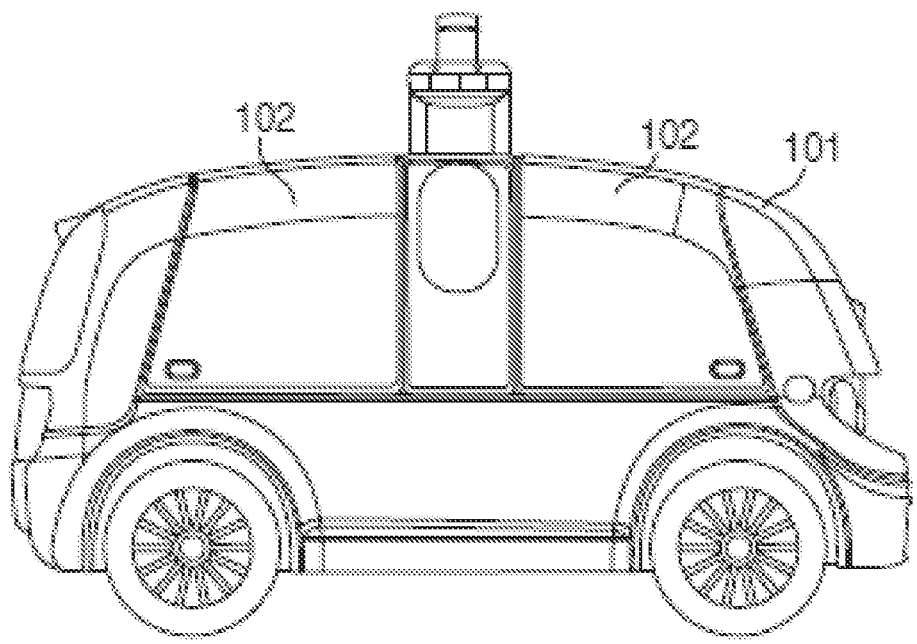
FIG. 2 is a diagrammatic representation of a side of an autonomous vehicle in accordance with an embodiment.

FIG. 2 is a diagrammatic representation of a side of an autonomous vehicle, e.g., one of autonomous vehicles 101 of FIG. 1, in accordance with an embodiment. Autonomous vehicle 101, as shown, is a vehicle configured for land travel. Typically, autonomous vehicle 101 includes physical vehicle components such as a body or a chassis, e.g., a frame, as well as conveyance mechanisms, e.g., wheels. In one embodiment, autonomous vehicle 101 may be relatively narrow, e.g., approximately two to approximately five feet wide, and may have a relatively low mass and relatively low center of gravity for stability. Autonomous vehicle 101 may be arranged to have a working speed or velocity range of between approximately one and approximately forty-five miles per hour (mph), e.g., approximately twenty-five miles per hour. In some embodiments, autonomous vehicle 101 may have a substantially maximum speed or velocity in range between approximately thirty and approximately ninety mph.

Autonomous vehicle 101 includes a plurality of compartments 102. Compartments 102 may be assigned to one or more entities, such as one or more customer, retailers, and/or vendors. Compartments 102 are generally arranged to contain cargo, items, and/or goods, and may be arranged to receive modular inserts (not shown) that allow the interior of compartments 102 to be configured for specific purposes, e.g., configured to support the administering of a medical test. Typically, compartments 102 may be secure compartments. It should be appreciated that the number of compartments 102 may vary. That is, although two compartments 102 are shown, autonomous vehicle 101 is not limited to including two compartments 102. In one embodiment, compartments 102 each include connections (not shown) which provide power and data connections in compartments 102, or to any inserts (not shown) which may be provided with power and/or commands and data.

Figure 3:
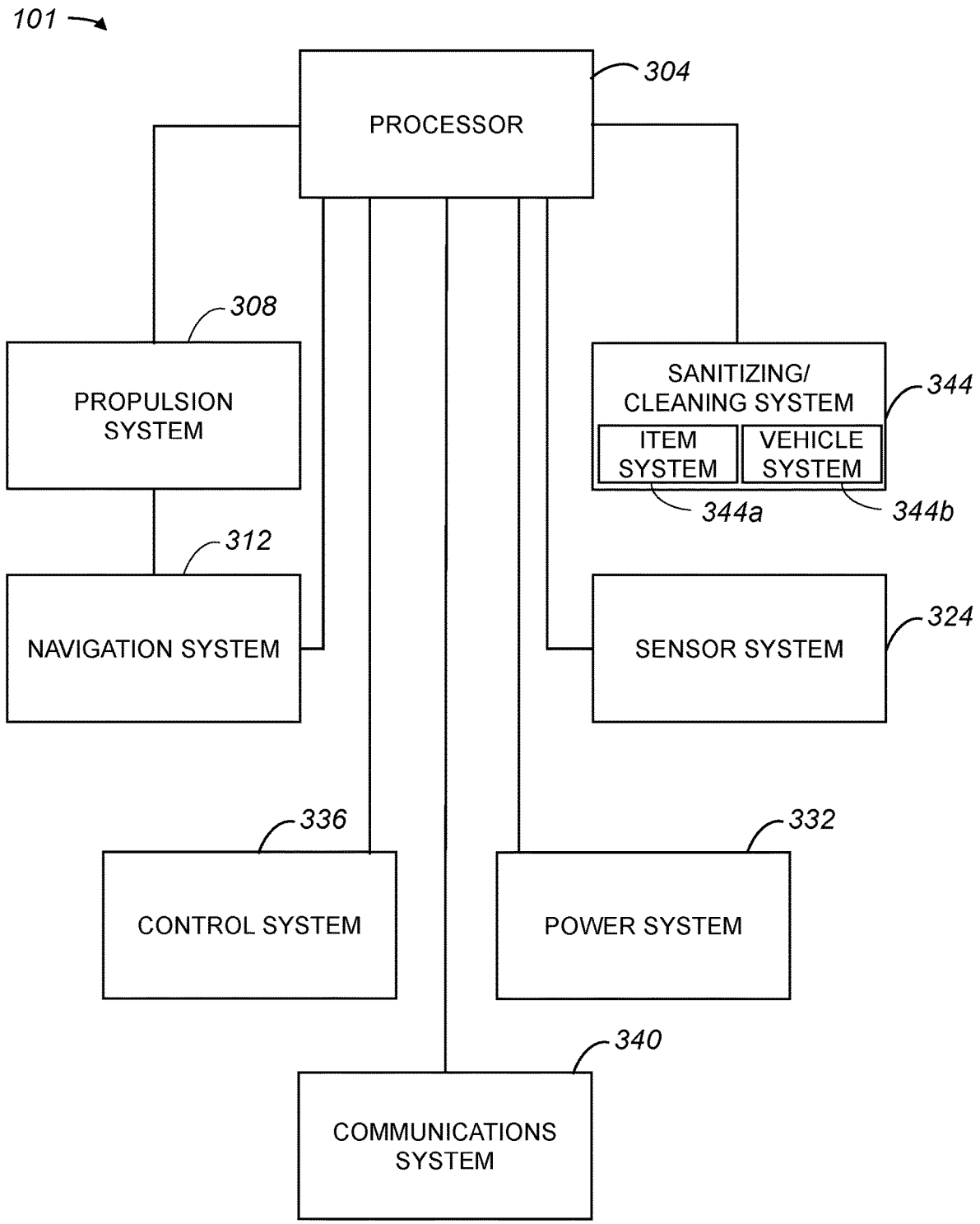
FIG. 3 is a block diagram representation of an autonomous vehicle in accordance with an embodiment.

FIG. 3 is a block diagram representation of an autonomous vehicle, e.g., autonomous vehicle 101 of FIG. 1, in accordance with an embodiment. An autonomous vehicle 101 includes a processor 304, a propulsion system 308, a navigation system 312, a sensor system 324, a power system 332, a control system 336, a communications system 340, and a sanitizing/cleaning system 344. It should be appreciated that processor 304, propulsion system 308, navigation system 312, sensor system 324, power system 332, communications system 340, and sanitizing/cleaning system 344 are all coupled to, or otherwise carried by, a chassis or body of autonomous vehicle 101.

Processor 304 is arranged to send instructions to and to receive instructions from or for various components such as propulsion system 308, navigation system 312, sensor system 324, power system 332, and control system 336. Propulsion system 308, or a conveyance system, is arranged to cause autonomous vehicle 101 to move, e.g., drive. For example, when autonomous vehicle 101 is configured with a multi-wheeled automotive configuration as well as steering, braking systems and an engine, propulsion system 308 may be arranged to cause the engine, wheels, steering, and braking systems to cooperate to drive. In general, propulsion system 308 may be configured as a drive system with a propulsion engine, wheels, treads, wings, rotors, blowers, rockets, propellers, brakes, etc. The propulsion engine may be a gas engine, a turbine engine, an electric motor, and/or a hybrid gas and electric engine.

Navigation system 312 may control propulsion system 308 to navigate autonomous vehicle 101 through paths and/or within unstructured open or closed environments. Navigation system 312 may include at least one of digital maps, street view photographs, and a global positioning system (GPS) point. Maps, for example, may be utilized in cooperation with sensors included in sensor system 324 to allow navigation system 312 to cause autonomous vehicle 101 to navigate through an environment.

Sensor system 324 includes any sensors, as for example LiDAR, radar, ultrasonic sensors, microphones, altimeters, and/or cameras. Sensor system 324 generally includes onboard sensors which allow autonomous vehicle 101 to safely navigate, and to ascertain when there are objects near autonomous vehicle 101. In one embodiment, sensor system 324 may include propulsion systems sensors that monitor drive mechanism performance, drive train performance, and/or power system levels. Sensor system 324 may be part of a perception system.

Power system 332 is arranged to provide power to autonomous vehicle 101. Power may be provided as electrical power, gas power, or any other suitable power, e.g., solar power or battery power. In one embodiment, power system 332 may include a main power source, and an auxiliary power source that may serve to power various components of autonomous vehicle 101 and/or to generally provide power to autonomous vehicle 101 when the main power source does not have the capacity to provide sufficient power.

Communications system 340 allows autonomous vehicle 101 to communicate, as for example, wirelessly, with a fleet management system (not shown) that allows autonomous vehicle 101 to be controlled remotely. Communications system 340 generally obtains or receives data, stores the data, and transmits or provides the data to a fleet management system and/or to autonomous vehicles 101 within a fleet 100. The data may include, but is not limited to including, information relating to scheduled requests or orders, information relating to on-demand requests or orders, and/or information relating to a need for autonomous vehicle 101 to reposition itself, e.g., in response to an anticipated demand.

Sanitizing/cleaning system 344 is generally arranged to sanitize, disinfect, sterilize, purify, decontaminate, and/or clean vehicle 101, as well as to clean items carried in vehicle 101, e.g., items contained within compartments 102 as shown in FIG. 2. It should be appreciated that when cleaning items carried in vehicle 101, sanitizing/cleaning system 344 may also clean the interior of compartments 102 and inserts in compartments 102 such as inserts that hold the items. Sanitizing/cleaning system 344 may include an item cleaning system 344a and a vehicle cleaning system 344b. Sanitizing/cleaning system 344 may draw power from power system 332, e.g., from a battery included in power system 332, or sanitizing/cleaning system 344 may include a substantially dedicated power source such as a dedicated battery.

Item cleaning system 344a is arranged to clean items or goods that are transported in a compartment of vehicle 101. Item cleaning system 344a may be arranged, in one embodiment, to disinfect items that are being delivered to a customer and mechanisms in a compartment of vehicle 101 including, but not limited to including, modular inserts arranged to hold the items, mechanical components arranged to facilitate the loading and/or unloading of the items, etc. Item cleaning system 344a may be arranged to disinfect items using ultraviolet (UV) light, heat, and/or chemicals.

Vehicle cleaning system 344b is arranged to clean vehicle 101, e.g., the exterior surfaces of vehicle 101. In one embodiment, vehicle cleaning system 344b may include a reservoir that holds water or a cleaning fluid, a dispensing mechanism such as a nozzle, and a wiper mechanism. It should be appreciated that vehicle cleaning system 344b may further being arranged to clean interior surfaces of vehicle 101 including, but not limited to including, the interior of a compartment of vehicle 101.

In some embodiments, control system 336 may cooperate with processor 304 to determine where autonomous vehicle 101 may safely travel, and to determine the presence of objects in a vicinity around autonomous vehicle 101 based on data, e.g., results, from sensor system 324. In other words, control system 336 may cooperate with processor 304 to effectively determine what autonomous vehicle 101 may do within its immediate surroundings. Control system 336 in cooperation with processor 304 may essentially control power system 332 and navigation system 312 as part of driving or conveying autonomous vehicle 101. Additionally, control system 336 may cooperate with processor 304 and communications system 340 to provide data to or obtain data from other autonomous vehicles 101, a management server, a global positioning server (GPS), a personal computer, a teleoperations system, a smartphone, or any computing device via the communication module 340. In general, control system 336 may cooperate at least with processor 304, propulsion system 308, navigation system 312, sensor system 324, and power system 332 to allow vehicle 101 to operate autonomously. That is, autonomous vehicle 101 is able to operate autonomously through the use of an autonomy system that effectively includes, at least in part, functionality provided by propulsion system 308, navigation system 312, sensor system 324, power system 332, and control system 336. Components of propulsion system 308, navigation system 312, sensor system 324, power system 332, and control system 336 may effectively form a perception system that may create a model of the environment around autonomous vehicle 101 to facilitate autonomous or semi-autonomous driving.

As will be appreciated by those skilled in the art, when autonomous vehicle 101 operates autonomously, vehicle 101 may generally operate, e.g., drive, under the control of an autonomy system. That is, when autonomous vehicle 101 is in an autonomous mode, autonomous vehicle 101 is able to generally operate without a driver or a remote operator controlling autonomous vehicle. In one embodiment, autonomous vehicle 101 may operate in a semi-autonomous mode or a fully autonomous mode. When autonomous vehicle 101 operates in a semi-autonomous mode, autonomous vehicle 101 may operate autonomously at times and may operate under the control of a driver or a remote operator at other times. When autonomous vehicle 101 operates in a fully autonomous mode, autonomous vehicle 101 typically operates substantially only under the control of an autonomy system.

Figure 4:
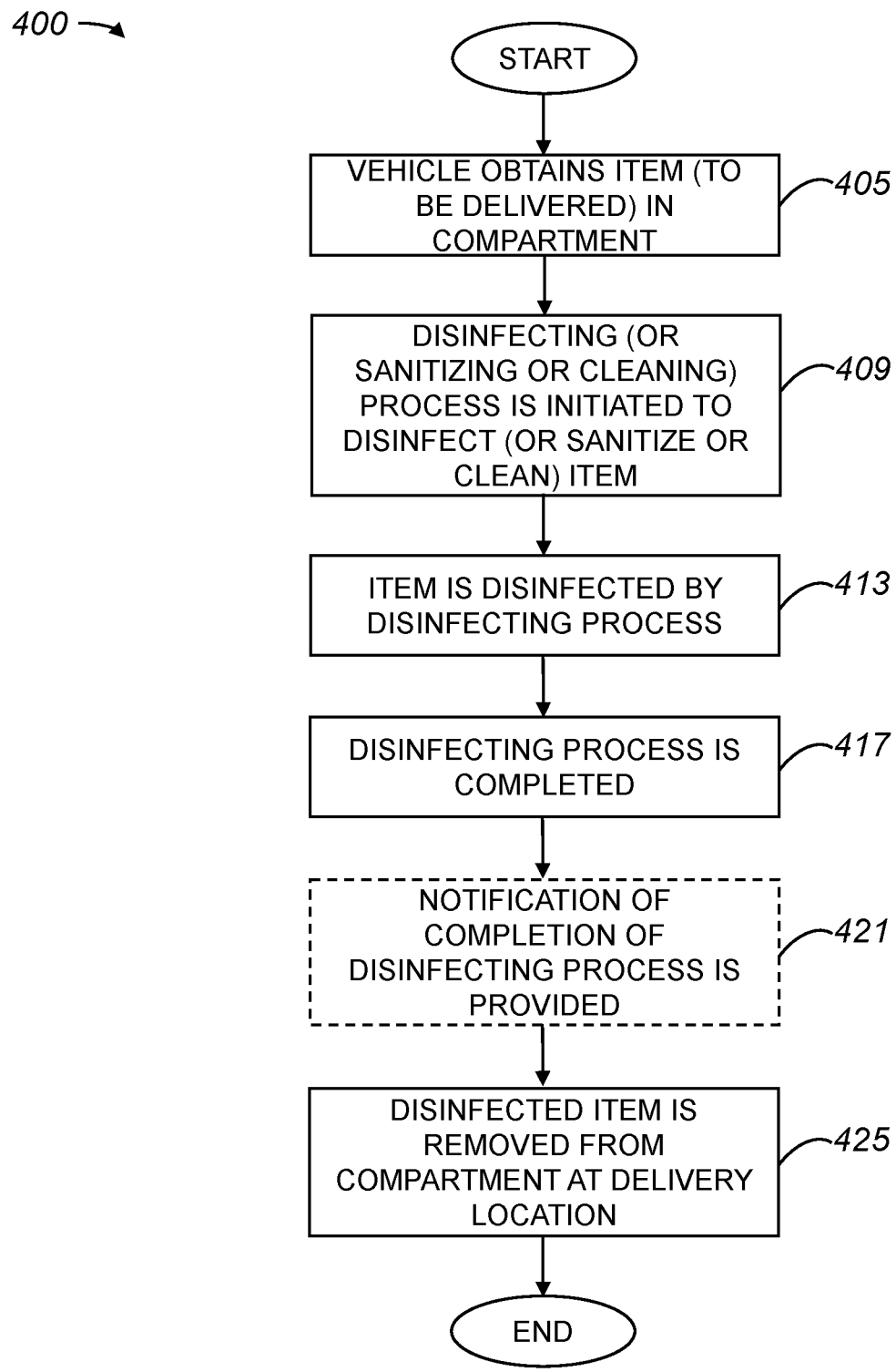
FIG. 4 is a process flow diagram which illustrates a method of disinfecting an item during a delivery in accordance with an embodiment.

The ability to disinfect or to otherwise clean an item that is carried in or transported in a compartment of autonomous vehicle 101 allows for contaminants to be removed from the item before the item is received by a customer. FIG. 4 is a process flow diagram which illustrates a method of disinfecting an item during a delivery in accordance with an embodiment. A method 400 of disinfecting an item during a delivery begins at a step 405 in which a vehicle, e.g., an autonomous vehicle, obtains an item that is to be delivered to a delivery location. The item may be received in a compartment of the vehicle.

Once the item is received in the compartment, a disinfecting or cleaning process is initiated in a step 409 to disinfect or to otherwise clean the item. A disinfecting or cleaning process may be initiated, in some instances, any time an item is received in a compartment. Such a process may be initiated substantially automatically, e.g., upon the item being placed in the compartment and the closing of a door on the compartment, or may be initiated at the request of a customer who ordered the item, e.g., when the customer sends a request either to a fleet management system or substantially directly to the vehicle. The process may include, but is not limited to including, utilizing one or more sensors associated with the vehicle to ascertain whether an item is placed within a compartment of the vehicle. Further, a disinfecting or cleaning process may be initiated at substantially any time between when a vehicle obtains an item and when the item is ready to be received by a customer when the vehicle arrives at a delivery location. In one embodiment, a disinfecting or cleaning process occurs while the vehicle is driving from a source destination to a delivery location.

The item is disinfected by a disinfecting process in a step 413. In general, a disinfecting process may be any suitable process which allows the item and, by extension, at least part of the compartment that the item is in, to be disinfected, sanitized, decontaminated, sterilized, purified, and/or otherwise cleaned. Processes may include, but are not limited to including, a process which involves the application of waves of any wavelength suitable for providing disinfecting capabilities such as light in the UV spectrum, a process which involves the application of heat, and/or a process which involves the application of chemicals such as disinfecting or cleaning agents.

In a step 417, the disinfecting process is completed. That is, in step 417, the item is disinfected or cleaned to a desired level. Factors which determine a desired level may vary widely. By way of example, the item may be considered to be disinfected based on an amount of time associated with the disinfecting process, a strength of a UV light, an amount of heat applied to the item, and/or a contaminant or pathogen level associated with the item. In one embodiment, a sensor may be located in a compartment of a vehicle, and arranged to detect a pathogen level. Such a sensor may detect a pathogen level at the time the item is placed in the compartment, and the pathogen level may be used to determine an amount of disinfecting or cleaning necessary to reach the desired level, or even whether a disinfecting or cleaning process is necessary.

In an optional step 421, a notification of a completion of a disinfecting process may be provided. Such a notification may be provided substantially directly to a customer, or to a fleet management system, to notify the customer that the item he or she ordered has been disinfected or cleaned. In one embodiment, measurement of contaminant or pathogen levels associated with the item that has been disinfected may be taken before and after the disinfecting process, and the notification may include a report which identifies the measurements.

From step 417 or from optional step 421, process flow moves to a step 425 in which the disinfected item is removed from the compartment on the vehicle at a delivery location. In other words, the disinfected item is delivered to a customer. After the disinfected item is delivered to a customer, the method of disinfecting an item during delivery is completed.

As mentioned above, while a disinfecting process may be substantially automatic, i.e., assumed to be requested as a default, a customer may be tasked with requesting a disinfecting process. For example, a customer may access a customer portal such as an online customer portal, or send a text to a particular number to activate a disinfecting process. In one embodiment, at least one camera may be installed in a compartment of a vehicle to allow a customer to watch a video or still feed from the camera while the disinfecting process is ongoing. Alternatively, in lieu of a customer requesting a disinfecting process, a retailer or vendor of an item may request a disinfecting process. When a provider of an item requests a disinfecting process, the provider and/or a customer may receive notifications relating to the disinfecting process.

Figure 5:
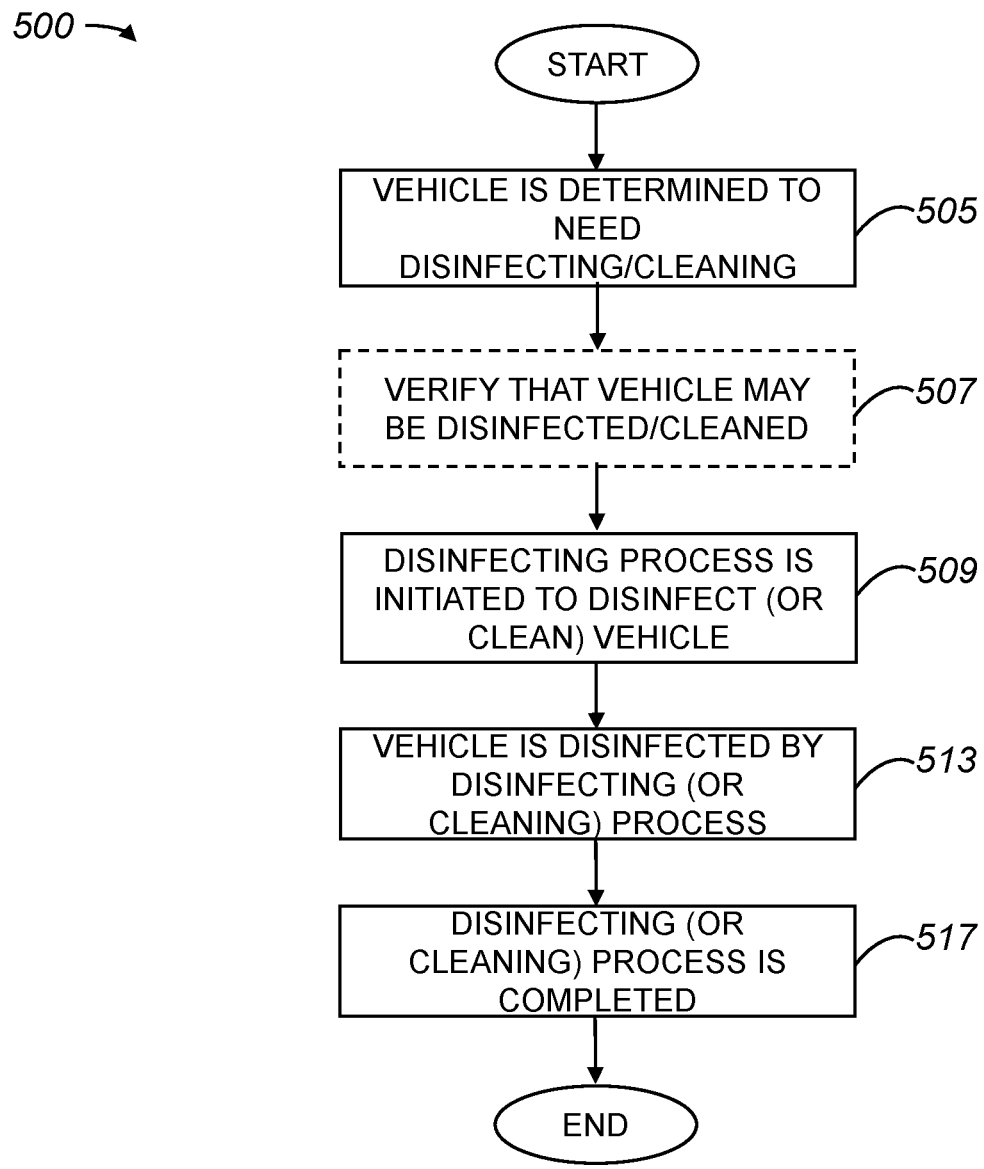
FIG. 5 is a process flow diagram which illustrates a method of disinfecting a vehicle in accordance with an embodiment.

It may be desirable to disinfect or sanitize a delivery vehicle periodically, or after each delivery is completed to decrease the likelihood that the vehicle itself may be carrying a contaminant or a pathogen. Disinfecting a delivery vehicle generally includes, but is not limited to including, disinfecting surfaces of delivery compartments of the vehicle and/or exterior surfaces of the vehicle. Referring next to FIG. 5, a method of disinfecting a vehicle will be described in accordance with an embodiment. A method 500 of disinfecting a vehicle begins at a step 505 in which it is determined that a vehicle needs disinfecting or cleaning. A vehicle may be identified as in need of disinfecting or cleaning using any suitable metric. Suitable metrics include, but are not limited to including, a contamination level present on an exterior of the vehicle as measured using sensors, an amount of time that has elapsed since a most recent disinfecting process, a number of deliveries made since a most recent disinfecting process, a number of customers serviced by the vehicle since a most recent disinfecting process, etc. Although the entire vehicle may be disinfected or cleaned in step 505, in some embodiments, different parts of the vehicle may be identified for cleaning and subsequently cleaned. For example, the doors of a compartment may be cleaned, a customer interface screen on the vehicle may be cleaned, and/or a windshield on the vehicle may be cleaned.

After it is determined that the vehicle would benefit from a disinfecting or cleaning process, it is verified in an optional step 507 whether the vehicle may be disinfected or cleaned. For example, a vehicle may be determined not to be in a situation in which cleaning of an exterior surface of the vehicle may be performed if there is an individual standing near the vehicle. The vehicle may also be determined not to be in a situation in which a compartment of the vehicle may be disinfected using a UV light source when a door to the compartment is open and/or when there is an individual standing near the vehicle. Verifying whether the vehicle may be disinfected or cleaned may include, but is not limited to including, readying the vehicle to be disinfected or cleaned, e.g., by warning a nearby individual to move and/or by closing doors to compartments.

Once it is determined that the vehicle would benefit from a disinfecting or cleaning process, and optionally if the vehicle is verified as being suitable to be disinfected or cleaned, a disinfecting process is initiated in a step 509. The disinfecting process may include the use of cleaning solutions and mechanical dispensing devices, as will be discussed below with reference to FIG. 7. The disinfecting process may be initiated substantially automatically upon a determination of a need for disinfecting, or the disinfecting process may be initiated substantially manually, e.g., through a fleet management system. In a step 513, the vehicle is disinfected by the disinfecting process. The disinfecting process may include one or more different methods. For example, one method may be used to disinfect a compartment of the vehicle, and another method may be used to disinfect an exterior surface of the vehicle. The disinfecting process is completed in a step 517, and upon completion of the disinfecting process, the method of disinfecting a vehicle is completed.

Figure 6A:
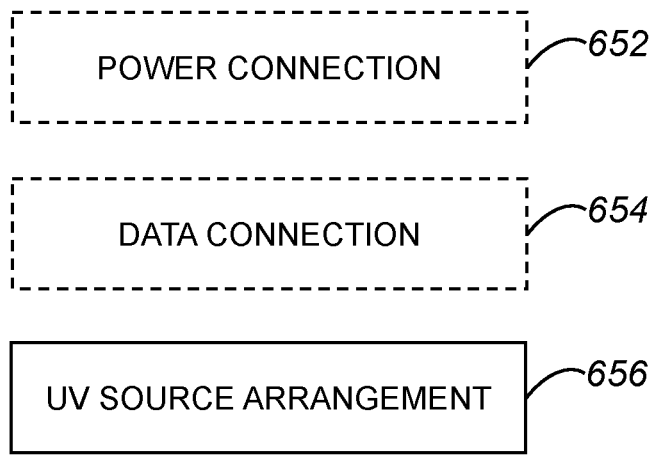
FIG. 6A is a block diagram representation of a first item cleaning system, e.g., item cleaning system 344a of FIG. 3, in accordance with an embodiment.
Figure 6B:
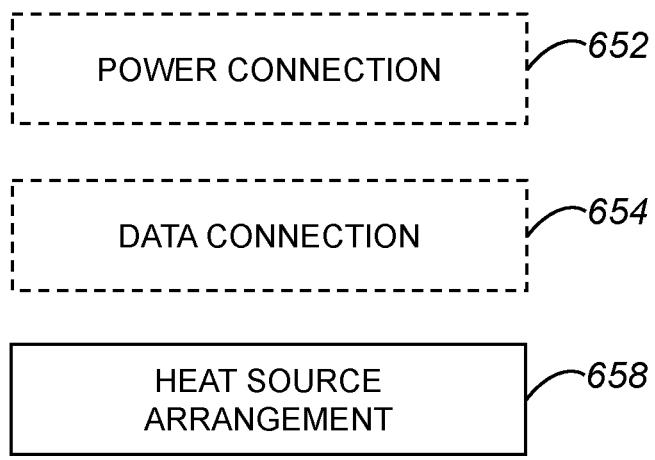
FIG. 6B is a block diagram representation of a second item cleaning system, e.g., item cleaning system 344a of FIG. 3, in accordance with an embodiment.
Figure 6C:
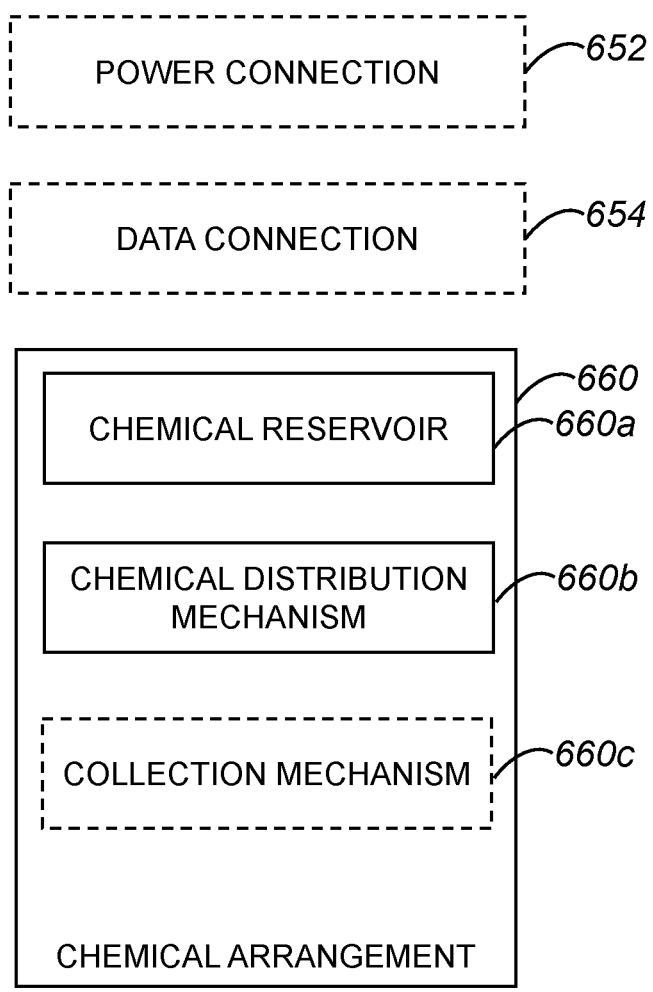
FIG. 6C is a block diagram representation of a third item cleaning system, e.g., item cleaning system 344a of FIG. 3, in accordance with an embodiment.

As discussed above with respect to FIG. 3, sanitizing/cleaning system 344 may generally include item cleaning system 344a and vehicle cleaning system 344b. With reference to FIGS. 6A-6C, examples of item cleaning system 344a will be described, and with reference to FIG. 7, an example of vehicle cleaning system 344b will be described.

FIG. 6A is a block diagram representation of a first item cleaning system, e.g., item cleaning system 344a of FIG. 3, in accordance with an embodiment. A first cleaning system 344a' may be substantially built into a compartment of a vehicle such as compartment 102 of autonomous vehicle 101 as described with respect to FIGS. 2 and 3. Alternatively, first cleaning system 344a' may be configured as an insert that is removably positioned in a compartment.

First cleaning system 344a' may include a power connection 652 that is arranged to draw power from a vehicle, and may be coupled to a power port on the vehicle. First cleaning system 344a' may also include a data connection 654 arranged to obtain data from and provide data to a vehicle, and may be coupled to a data port on the vehicle.

A UV source arrangement 656 is included in first cleaning system 344a', and generally provides UV light that disinfects items such as items which are positioned in a compartment of a vehicle that also contains first cleaning system 344a'. UV source arrangement 656 may be, for example a UV sterilizer wand, one or more UV light sources, a UV sterilizer box, a UV sterilizer oven, and/or a UV sterilizer chamber. In general, UV source arrangement 656 may be any suitable component that is arranged to emit UV light. UV source arrangement 656 may also include a controller which allows for control of when to emit UV light, how long to emit the UV light, and/or how much UV light to emit.

UV source arrangement 656 may be configured to provide UV light at a wavelength that is suitable for substantially kill, or deactivate, pathogens such as bacteria and viruses. The wavelengths of UV waves used to kill or to deactivate pathogens may vary widely depending upon factors including but not limited to including, the types of pathogens which are to be killed or deactivated. In one embodiment, UV source arrangement 656 may be a UVC source, and the wavelength of light emitted by the UVC source may between approximately 200 nanometers (nm) and approximately 300 nm, e.g., approximately 222 nm.

FIG. 6B is a block diagram representation of a second item cleaning system, e.g., item cleaning system 344a of FIG. 3, in accordance with an embodiment. A second cleaning system 344a" may be substantially built into a compartment of a vehicle, or may alternatively be configured as an insert that is removably positioned in a compartment. Second cleaning system 344a" may include power connection 652 and/or data connection 654.

A heat source arrangement 658 is included in second cleaning system 344a", and generally provides heat at a temperature and an amount that is sufficient to disinfect or to otherwise clean an item. Heat source arrangement 658 may include any suitable heat source including, but not limited to including, a heat source which includes a mixture of chemicals which cooperate to generate heat, an electric heater, a gas heater, a steam sterilizer such as an autoclave, and/or the like. Heat source arrangement 658 may also include a controller that may be used to control when heat is to be applied, how long to apply the heat, and/or how much heat to apply. In one embodiment, heat source arrangement 658 may include a fan configured to facilitate the spread of heated air within a compartment or space.

Second cleaning system 344a" may be configured as an autoclave. When second cleaning system 344a" is an autoclave, heat source arrangement 658 may be arranged to generate steam to perform steam sterilization to disinfect or otherwise clean an item. When second cleaning system 344a" is an autoclave, the temperature within second cleaning system 344a" may be any suitable temperature that allows for steam sterilization. By way of example, the temperature may be approximately 250 degrees Fahrenheit (F) or higher. In one embodiment, the temperature may be less than approximately 275 degrees F. It should be appreciated that while performing a disinfecting process such as a steam sterilization, second cleaning system 344a" may be arranged to maintain a suitable temperature for a predetermined amount of time. Such a predetermined amount of time may vary widely, and may depend upon factors including, but not limited to including, the temperature to be maintained by second cleaning system 344a″, the type of item that is being disinfected, and/or the size of the item that is being disinfected.

In one embodiment, heat source arrangement 658 may be a source of heat within a vehicle which generates heat as a byproduct. By way of example, systems on a vehicle such as a refrigeration system may generate heat while providing cooling. Such generated heat may be used in second cleaning system 344a″.

FIG. 6C is a block diagram representation of a third item cleaning system, e.g., item cleaning system 344a of FIG. 3, in accordance with an embodiment. A third cleaning system 344a‴ may be substantially built into a compartment of a vehicle, or may alternatively be configured as an insert that is removably positioned in a compartment. Third cleaning system 344a‴ may include power connection 652 and/or data connection 654.

A chemical arrangement 660 is included in third cleaning system 344a‴, and includes a chemical reservoir 660a and a chemical distribution mechanism 660b. Chemical reservoir 660a is arranged to contain chemical solutions, e.g., chemicals that form a cleaning or disinfecting fluid. Such chemical solutions may include, but are not limited to including, alcohol, sanitizer, soap, ammonium chloride, and/or hydrogen peroxide. Chemical distribution mechanism 660b may any suitable mechanism which allows the contents of chemical reservoir 660a to be dispersed or otherwise applied to disinfect or clean an item. Suitable mechanisms include, but are not limited to including, a nozzle arrangement, a sprinkler arrangement, a spray arrangement, and/or a pump arrangement. In one embodiment, a spray arrangement may be arranged to spray a mist that is made up of a chemical solution. Chemical arrangement 660 may also include a controller that may be used to control when chemical distribution mechanism 660b is to be activated, how long to keep chemical distribution mechanism 660b active, and/or the amount of chemicals to disperse.

Chemical arrangement 660 may include an optional collection mechanism 660c. Optional collection mechanism 660c may be arranged to collect chemicals after the chemicals are distributed. For example, after chemicals dispersed by chemical distribution mechanism 660b contact surfaces to disinfect or clean the surfaces, the chemicals may be collected by optional collection mechanism 660c. By collecting chemicals, the chemicals are prevented from substantially pooling up or otherwise collecting in a compartment of a vehicle. Optional collection mechanism 660c may be configured as a tank or a reservoir Alternatively, collection mechanism 660c may include a drain. Such a drain may be configured to funnel chemicals to a reservoir that is external to, e.g., not part of but coupled to, third cleaning system 344a‴.

Figure 7:
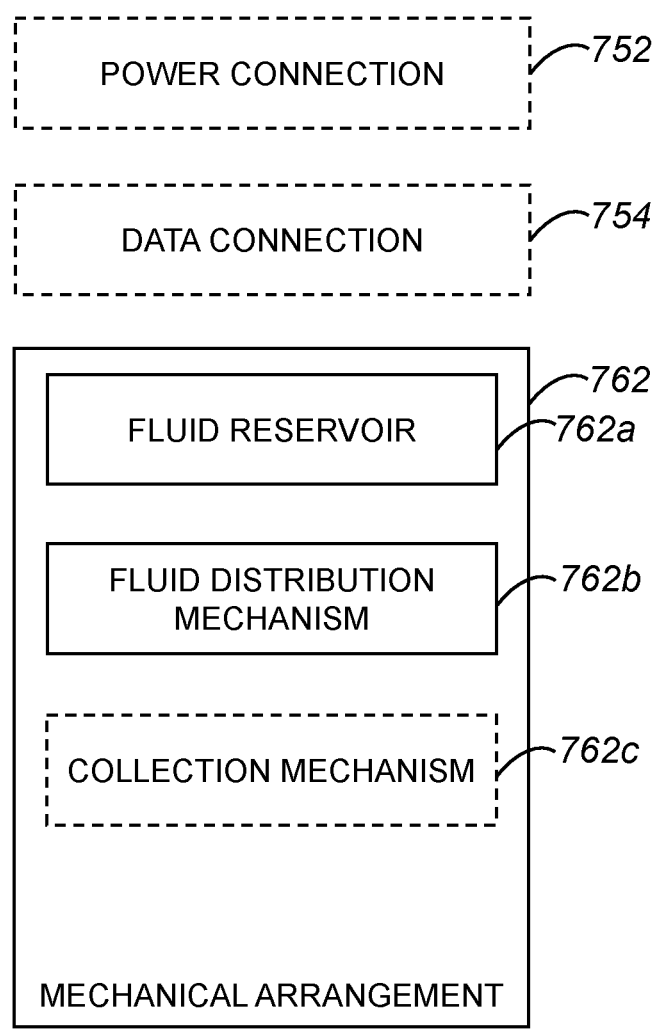
FIG. 7 is a block diagram representation of a vehicle cleaning system, e.g., vehicle cleaning system 344b of FIG. 3, in accordance with an embodiment.

FIG. 7 is a block diagram representation of a vehicle cleaning system, e.g., vehicle cleaning system 344b of FIG. 3, in accordance with an embodiment. Vehicle cleaning system 344b may include a power connection 752 and a data connection 754. In the described embodiment, vehicle cleaning system 344b includes a mechanical arrangement 762 which has a fluid reservoir 762a, which is arranged to contain a fluid that may be used to clean a surface of a vehicle, and a fluid distribution mechanism 762b, which is arranged to distribute the fluid. Mechanical arrangement 762 may be positioned substantially anywhere on a vehicle, e.g., on exterior surfaces of the vehicle. When mechanical arrangement 762 is positioned on at least one exterior surface of the vehicle, contaminants present on the exterior surface may be removed from the surface. Fluid reservoir 762a may contain a disinfecting solution, or any other solution that may be used for cleaning purposes. Fluid distribution mechanism 762b may include a mechanism that removes the disinfecting solution from fluid reservoir 762a and disperses the disinfecting solution. Dispersing the disinfecting solution may include, but is not limited to including, spraying the disinfecting solution on an exterior of a vehicle and activating a wiper or a squeegee as a part of an overall disinfecting process. In general, mechanical arrangement 762 may also include a controller that controls the distribution of a disinfecting solution and the activation of fluid distribution mechanism 762b.

Mechanical arrangement 762 is not limited to spraying a fluid or a liquid in order to clean a vehicle. It should be appreciated that fluid reservoir 762a may, in one embodiment, contain air while fluid distribution mechanism 762b may include a fan or other air blower which blows the air over a surface of a vehicle to clean the vehicle.

In one embodiment, fluid distributed by fluid distribution mechanism 762b may be collected after a surface of a vehicle is cleaned. When the fluid does not evaporate, does not vaporize, and/or is not dispersed into an environment surrounding the vehicle, the vehicle may be collected by an optional collection mechanism 762c of mechanical arrangement 762. Optional collection mechanism 762c may include, but is not limited to including, channels, tubes, ducts, tanks, and/or reservoirs arranged to collect and to hold a fluid such as a disinfecting solution that is dispensed or distributed as part of a disinfecting or cleaning process.

Cleaning a delivery vehicle and disinfecting items delivered by the delivery vehicle may allow for the safe delivery of the items to a customer without the customer having to worry about contaminants being present on the items. To further put a customer at ease, a delivery vehicle may be arranged such that the customer may retrieve items from a compartment of the delivery vehicle substantially without physically touching the vehicle. That is, physical contact between a customer and a delivery vehicle may be substantially minimized. For example, a door on a compartment of a delivery vehicle may open automatically, or the door may be triggered to open by an action the customer takes without physically touching the vehicle.

Figure 8A:
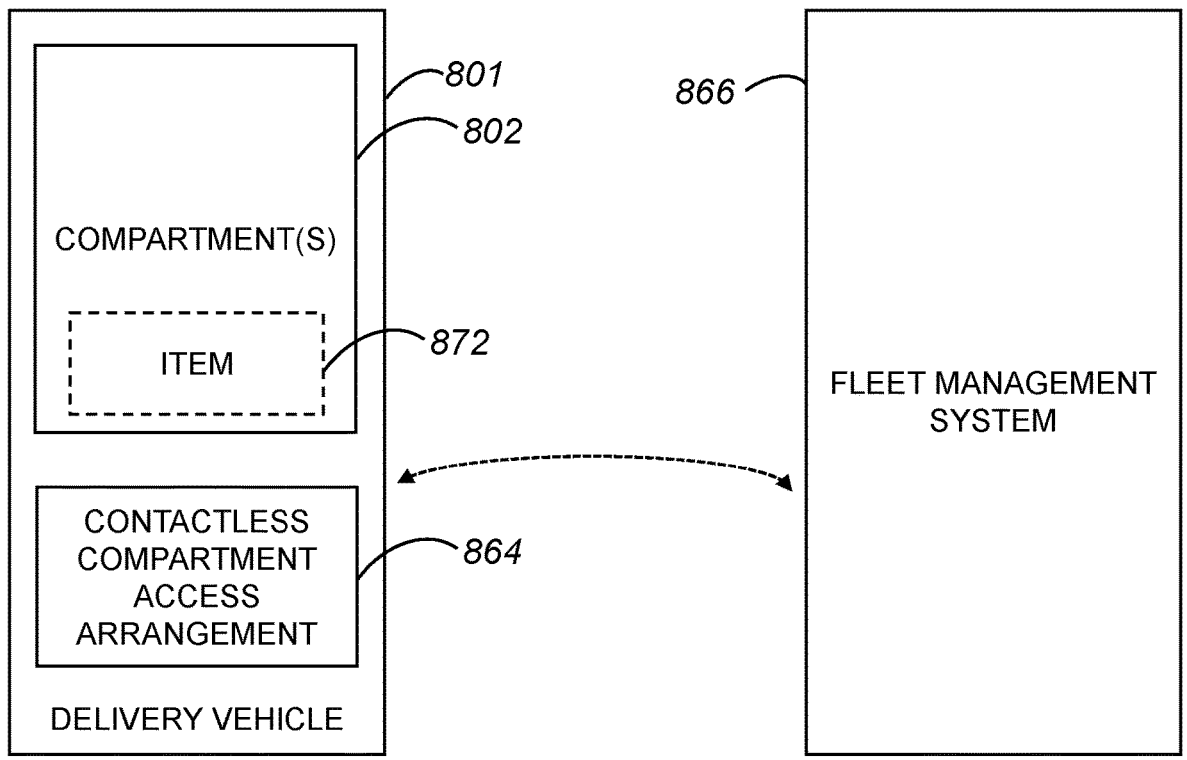
FIG. 8A is a diagrammatic representation of a delivery vehicle with a contactless compartment access arrangement that is utilized by a fleet management system to allow access to a compartment in accordance with an embodiment.

Referring next to FIG. 8A, a delivery vehicle with a contactless compartment access arrangement that is utilized by a fleet management system to allow a customer to access to a compartment of the vehicle will be described in accordance with an embodiment. A vehicle 801, which may be an autonomous vehicle, includes at least one compartment 802 in which an item 872 that is being delivered may be contained.

Compartment 802 is arranged to be accessed in a contactless manner. That is, a customer may access compartment 802 to retrieve item 872 without having to make physical contact with vehicle 801. A contactless compartment access arrangement 864 may be a part of vehicle 801, and may be arranged to communicate with a fleet management system 866 to cause compartment 802 to be opened, e.g., to unlock and open a door on compartment 802. Fleet management system 866 may generally be arranged to coordinate deliveries and to support deliveries made by a fleet of vehicles such as vehicle 801. Fleet management system 866 may, in one embodiment, determine that vehicle 801 is ready to complete the delivery of item 872, and may communicate with contactless compartment access arrangement 864 to effectively provide instructions to open compartment 802. Upon receiving instructions from fleet management system 866, contactless compartment access arrangement 864 may cause compartment 802 to be opened, e.g., to cause a door on compartment 802 to be unlocked and opened. As will be appreciated by those skilled in the art, any suitable types of communications may be used to enable vehicle 801 to communicate with fleet management system 866. For example, wireless communications such as cellular communications, Wi-Fi communications, Bluetooth communications, and/or 3G/4G/5G communications may be used.

Figure 8B:
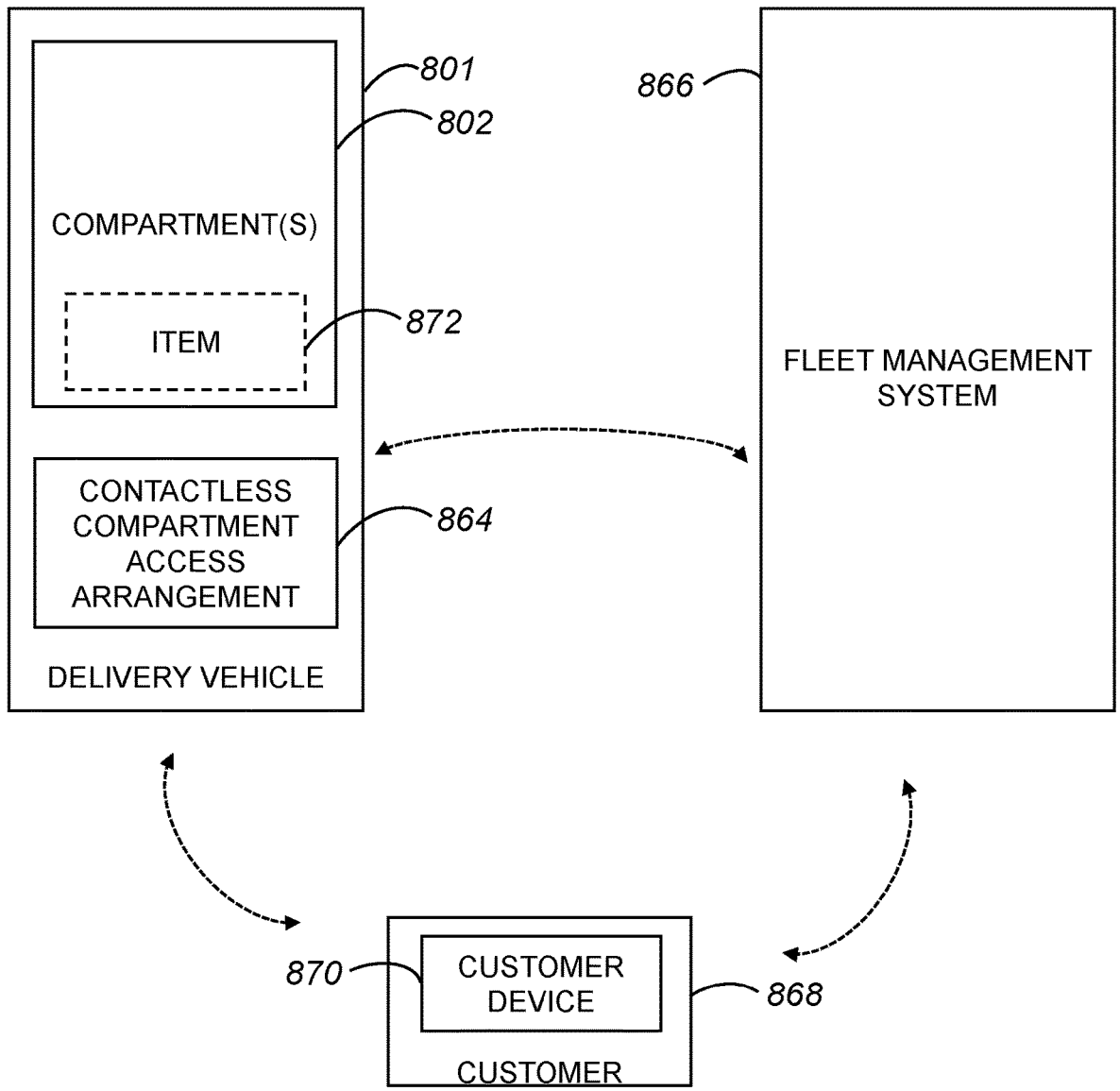
FIG. 8B is a diagrammatic representation of a delivery vehicle, e.g., delivery vehicle 801 of FIG. 8A, in which a contactless compartment access arrangement is arranged to be utilized by a customer and/or a fleet management system, e.g., fleet management system 866 of FIG. 8A, in accordance with an embodiment.

In one embodiment, a customer may substantially directly cause compartment 802 to open without physically touching vehicle 801. FIG. 8B is a diagrammatic representation of delivery vehicle 801 in which contactless compartment access arrangement 864 is arranged to be utilized by a customer and/or fleet management system 866 in accordance with an embodiment. A customer 868, who may have a customer device 870 such as a smartphone, a cell phone, a tablet computer, a laptop computer, or a desktop computer, may use device 870 to substantially directly instruct contactless compartment access arrangement 864 to provide access to compartment 802. Device 870 may engage in cellular communications, Wi-Fi communications, Bluetooth communications, and/or 3G/4G/5G with vehicle 801. For example, device 870 may send a text which causes compartment 802 to become accessible, or device 870 may be used to access an application or a web interface which allows customer 868 to effectively control the opening of compartment 802. It should be appreciated that in some embodiments, customer 868 may be expected to undergo an authorization or authentication process to verify his or her identity before being allowed access to item 872 or, more generally, compartment 802.

Alternatively, device 870 may communicate with fleet management system 866, as for example using communications such as cellular communications, Wi-Fi communications, Bluetooth communications, and/or 3G/4G/5G communications. Fleet management system 866 may communicate substantially directly with vehicle 801 to provide access to compartment 802 once device 870 communicates with fleet management system 866.

In one embodiment, contactless compartment access arrangement 864 may be arranged to provide access to compartment 802 based upon physical actions of customer 868. Contactless compartment access arrangement 864 may include at least one sensor arranged to enable customer 868 to gain access to compartment 802. Suitable sensors include, but are not limited to including, motion sensors, cameras, RFID readers, and/or microphones. A motion sensor may sense when customer 868 is making a motion intended to cause compartment 802 to become accessible, e.g., customer 868 may wave at the motion sensor or may kick a foot under a motion sensor. A camera may be used to verify the identity of customer 868, and to open a door to compartment 802 when customer 868 is determined to be in close proximity to vehicle 801. An RFID reader may be used to scan an ID card or badge in the possession of customer 868, and to enable access to compartment 802 upon authenticating the ID card or badge. NFC technology may also be used to open a door to compartment 802 when customer 868 presents his or her smartphone. A microphone may be used to pick up voice commands from customer 868 such as a spoken password. A text or SMS message may be sent by customer 868, or an online customer portal may be used by customer 868, to cause the door to compartment 802 to open.

Figure 9:
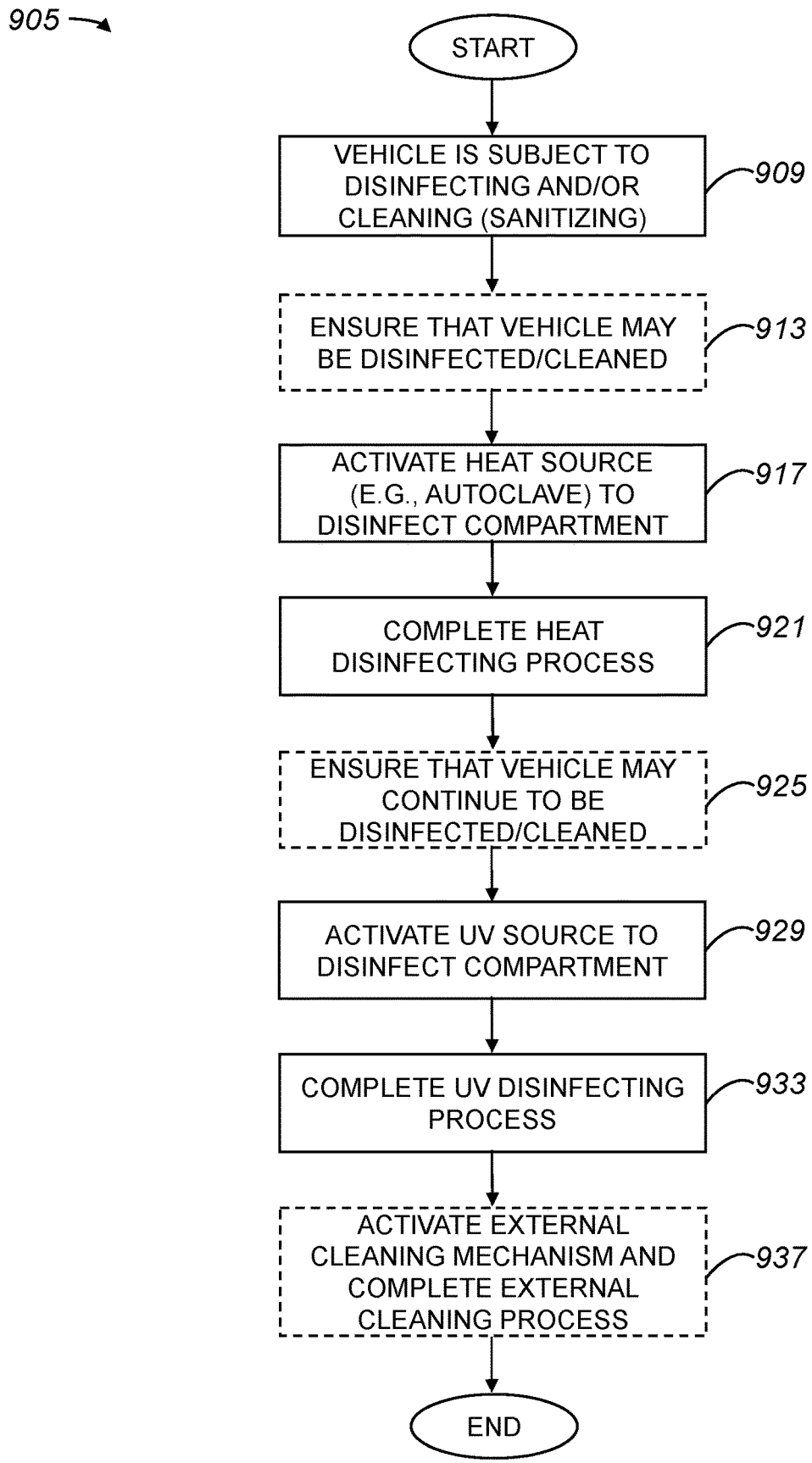
FIG. 9 is a process flow diagram which illustrates a first method of disinfecting and/or cleaning a vehicle using more than one disinfecting and/or cleaning process in accordance with an embodiment.

Some vehicles may have the capability of utilizing more than one disinfecting or cleaning process to disinfect or to clean surfaces associated with the vehicles. For example, an autonomous vehicle may be configured to utilize both heat and UV light to sanitize a compartment. Further, such an autonomous vehicle may be configured to also utilize chemical disinfectants to sanitize surface of the vehicle. With reference to FIG. 9, a method of disinfecting and/or cleaning a vehicle using more than one disinfecting and/or cleaning process will be described in accordance with an embodiment. A method 905 of disinfecting a vehicle which is configured to be disinfected or cleaned using at least heat and UV light begins at a step 909 in which it is determined that the vehicle is subject to being disinfected and/or cleaned. That is, it is identified that a vehicle is to be disinfected and/or cleaned. Such an identification may be made by the vehicle, as for example upon sensing that a compartment is contaminated or upon completing a delivery, or such an identification may be made through a fleet management system which is responsible for dispatching the vehicle. In one embodiment, a vehicle may be determined to be subject to disinfecting and/or cleaning when a customer requests that a compartment arranged to transport an item to the customer be disinfected. In another embodiment, a vehicle may be determined to be subject to disinfecting and/or cleaning when an item onboard the vehicle, e.g., in a compartment of the vehicle, is to be disinfected and/or cleaned.

Once a vehicle is determined to be subject to disinfecting and/or cleaning, in an optional step 913, it may be ensured that the vehicle is in a state that enables disinfecting and/or cleaning. Ensuring that the vehicle may be disinfected and/or cleaned includes, but is not limited to including, identifying whether there are humans or objects near the vehicle, prompting anyone or anything near the vehicle to move away from the vehicle, ensuring that doors on vehicle compartments are in a substantially closed position, ensuring that the vehicle has sufficient resources to perform the disinfecting and/or cleaning, and/or ensuring that the vehicle is in a physical location at which the vehicle may be safely disinfected and/or cleaned. Ensuring that the vehicle may be disinfected and/or cleaned may generally involve causing the vehicle to be substantially ready to be disinfected and/or cleaned, e.g., by closing compartment doors and by ensuring that there are no humans or objects in the vicinity of the vehicle.

From step 909, or from optional step 913, process flow moves to a step 917 in which a heat source is activated to disinfect a compartment on the vehicle. For example, an autoclave may be activated to provide heat to disinfect surfaces within the compartment. Alternatively, a heating, ventilation, and air conditioning (HVAC) system on the vehicle may be activated to provide heat within a compartment that is sufficient to disinfect surfaces within the compartment.

In a step 921, the heat disinfecting process initiated in step 917 is completed. After the heat disinfecting process is completed, in an optional step 925, it is ensured that the vehicle may continue to be disinfected and/or cleaned. For example, in optional step 925, it may be determined if there are people and/or objects that are near the vehicle and may be adversely affected by any UV waves emitted by the vehicle. In addition, in optional step 925, the vehicle may ensure that the temperature within the compartment is within a temperature range suitable for performing a UV disinfecting process and/or that any steam generated during the heat disinfecting process has been substantially cleared.

From step 921, or from optional step 925, process flow proceeds to a step 929 in which a UV source within a compartment of the vehicle is activated to disinfect surfaces within the compartment. The UV disinfecting process initiated in step 929 is completed in a step 933. One suitable UV disinfecting process will be discussed below with reference to FIGS. 14A and 14B.

Once a UV disinfecting process is completed, in an optional step 937, an external cleaning mechanism may be performed to clean at least one exterior surface of the vehicle. Activating an external cleaning mechanism may include, but is not limited to including, causing a cleaning fluid to be sprayed by the vehicle onto an exterior surface of the vehicle, causing the vehicle to apply heat to an exterior surface of the vehicle, and/or causing the vehicle to blow or to otherwise direct air over an exterior surface of the vehicle. Upon completing a UV disinfecting process in step 933, or upon completing an external cleaning process in optional step 937, the method of disinfecting a vehicle which is configured to be disinfected or cleaned using at least heat and UV lights is completed.

Figure 10:
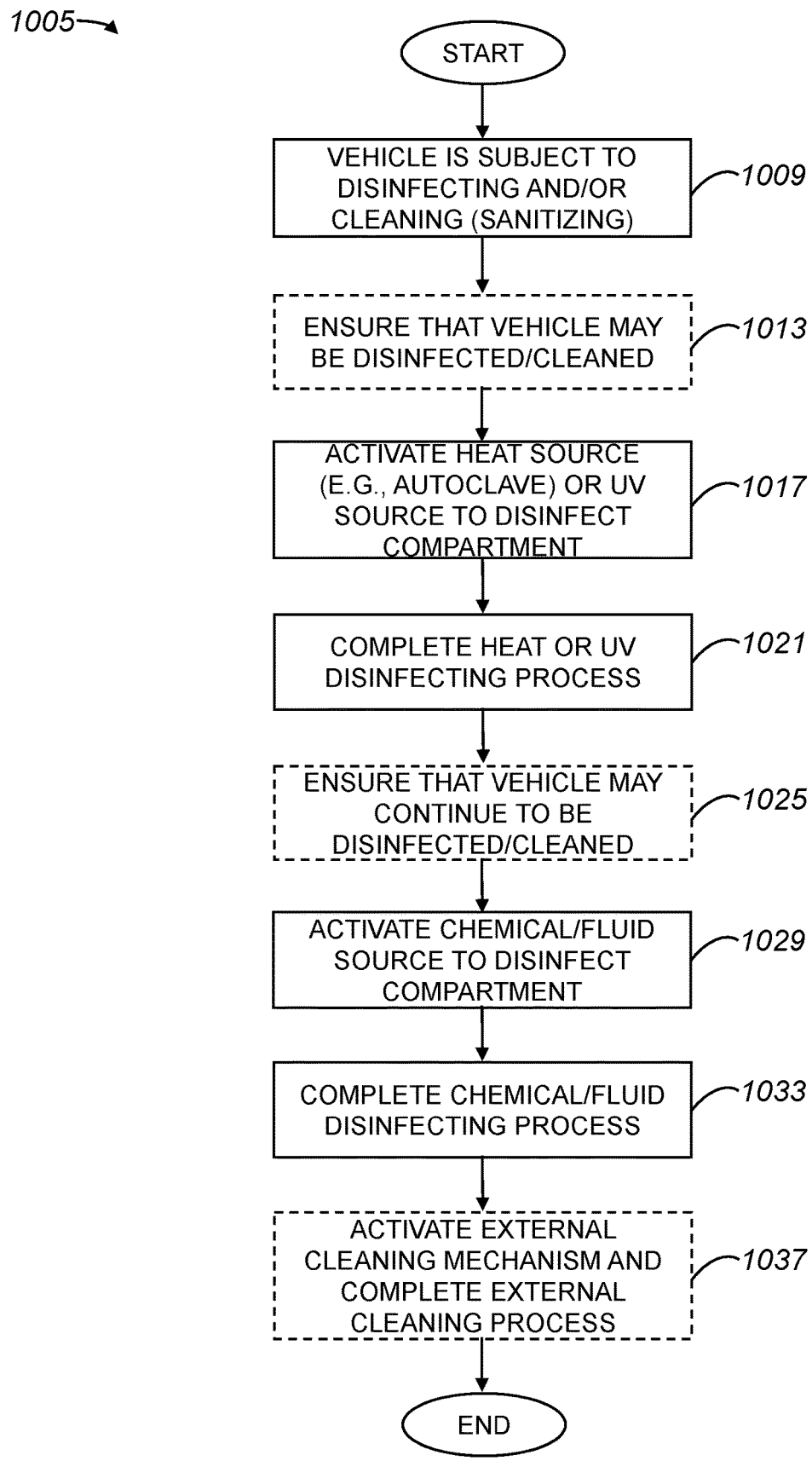
FIG. 10 is a process flow diagram which illustrates a second method of disinfecting and/or cleaning a vehicle using more than one disinfecting and/or cleaning process in accordance with an embodiment.

When a vehicle is configured to include more than one vehicle cleaning mechanism, one of the mechanisms included may utilized chemicals or fluids for disinfecting and/or cleaning. For example, after a contaminant such as a virus is inactivated using heat and/or UV waves within a compartment, it may be desirable to substantially wash away the contaminant such that the contaminant, although inactive, is not present in the compartment. FIG. 10 is a process flow diagram which illustrates a method of disinfecting and/or cleaning a vehicle using more than one disinfecting and/or cleaning process in which a chemical or fluid is involved in accordance with an embodiment. A method 1005 of disinfecting a vehicle which is configured to be disinfected or cleaned using more than one method including a chemical and/or fluid cleaning method begins at a step 1009 in which it is determined that the vehicle is subject to being disinfected and/or cleaned.

Once a vehicle is determined to be subject to disinfecting and/or cleaning, in an optional step 1013, it may be ensured that the vehicle is in a state that enables disinfecting and/or cleaning. From step 1009, or from optional step 1013, process flow moves to a step 1017 in which a heat source and/or a UV source may be activated to disinfect a compartment on the vehicle. For example, an autoclave may be activated to provide heat to disinfect surfaces within the compartment or UV lights may be activated. When more than one source is activated, the sources may be activated substantially in series or substantially in parallel.

In a step 1021, the heat and/or UV disinfecting process initiated in step 1017 is completed. After the heat and/or UV disinfecting process is completed, in an optional step 1025, it is ensured that the vehicle may continue to be disinfected and/or cleaned.

From step 1021, or from optional step 1025, process flow proceeds to a step 1029 in which a chemical distribution system, e.g., a disinfecting or cleaning system which utilizes chemicals, within a compartment of the vehicle is activated to disinfect surfaces within the compartment. Chemical distribution system may be arranged to distribute chemicals to effectively wash away contaminants which have been substantially inactivated using heat and/or UV waves. The chemicals may include, but are not limited to including, disinfecting solutions such as alcohol, bleach, hydrogen peroxide, benzalkonium chloride, and/or water. It should be appreciated that chemicals may be distributed or dispersed as a fluid, a vapor, and/or a solid, e.g., in particulate form. The chemical and/or fluid disinfecting process initiated in step 1029 is completed in a step 1033.

Once a chemical and/or fluid disinfecting process is completed, in an optional step 1037, an external cleaning mechanism may be performed to clean at least one exterior surface of the vehicle. After completing a chemical and/or fluid disinfecting process in step 1033, or upon completing an external cleaning process in optional step 1037, the method of disinfecting a vehicle which is configured to be disinfected or cleaned using more than one method including a chemical and/or fluid cleaning method is completed.

Various systems which facilitate the sanitizing, disinfecting, and/or cleaning of a compartment onboard a vehicle may be located within the compartment. Components of such systems may be built into or mounted to walls of the compartment such that an interior space within the compartment may be sanitized, disinfected, and/or cleaned. In addition, the components may facilitate the sanitizing, disinfecting, and/or cleaning of items carried within the compartment.

Some vehicles may have an interior space which may support multiple types of sanitizing methods. For example, a vehicle may have a compartment in which supports both UV sanitization and heat sanitization. When more than one type of sanitization is supported, the selection of which type of sanitization to use may be based on a variety of different factors including, but not limited to including, the type of object that is to be sanitized, the shape of the object that is to be sanitized, the size of the object that is to be sanitized, the surface quality of the object that is to be sanitized, an amount of sanitization that is desired, an ambient temperature of an environment outside of the vehicle, a timing associated with sanitization, and safety associated with sanitization. An object with an irregular shape may, for instance, benefit from heat sanitization because UV light associated with UV sanitization may not be able to sanitize folds, pits, etc. in the object. Some objects may be suitable for heat sanitization, whereas some objects such as certain food items may not be suitable for heat sanitization.

When an ambient temperature outside of a vehicle is relatively hot, the use of heat sanitization may not be appropriate because the vehicle may overheat. Alternatively, when an ambient temperature outside of a vehicle is relatively cold, the use of heat sanitization may not be appropriate because heat sanitization may consume relatively high amounts of energy from a battery in order to reach a sanitization temperature, which may have an adverse effect on the operational range of the vehicle. One sanitization method may be selected for use, for example, when a vehicle is in transit, and another sanitization method may be selected for use when the vehicle is substantially stationary to substantially prevent overheating of the vehicle.

In one embodiment, an amount of time that is appropriate for a sanitization process to be completed may factor into a determination of which type of sanitization process to implement. An amount of time that is appropriate to reach a sterilization temperature, or an amount of time that is appropriate for UV lights to relatively reliably sterilize and object, may be impractical, e.g., too long. As such, a sanitization process may be selected based at least in part upon how long it may take for sanitization to be completed.

When safety is considered when selecting a sanitization process, there may be scenarios in which a human may access an area to be cleaned. When a human may access an area, e.g., readily open a compartment to expose an interior volume, UV sanitization may be substantially avoided to reduce the chance of injury to a human. It should be appreciated, however, the measures may be made to reduce the likelihood of injury to a human by substantially cutting power to UV sources and/or heat sources when the opening of a compartment door is sensed, or when a human is detected in the vicinity of a compartment door.

Figure 11A:
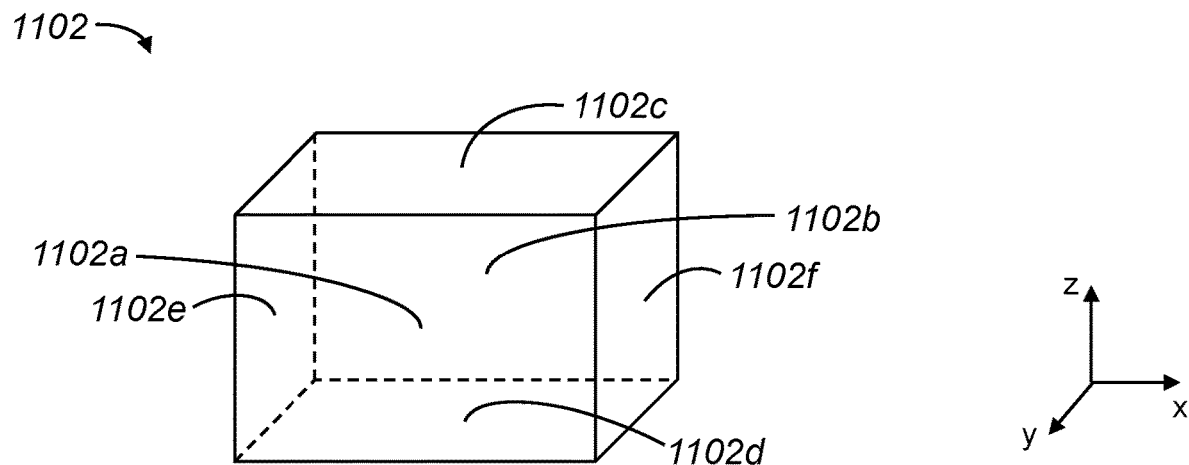
FIG. 11A is a diagrammatic representation of compartment of an autonomous vehicle in accordance with an embodiment.

FIG. 11A is a diagrammatic representation of compartment of an autonomous vehicle in accordance with an embodiment. A compartment 1102 of a vehicle may generally be defined by sides or walls 1102a-f which effectively define a volume or a space. Compartment 1102 is represented as a three-dimensional substantially rectangular object for ease of illustration.

Walls 1102a-f of compartment include a front wall 1102a, a back wall 1102b, a top wall or ceiling 1102c, a bottom wall or base 1102d, a first side wall 1102e, and a second side wall 1102f. In one embodiment, front wall 1102a may be a door that may be opened and closed, and/or unlocked and locked, to enable the interior volume of compartment 1102 to be accessed.

Figure 11B:
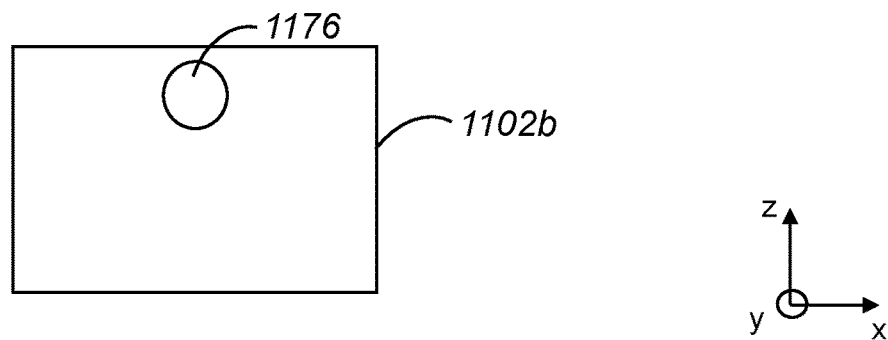
FIG. 11B is a diagrammatic representation of a wall of a compartment, e.g., compartment 1102 of FIG. 11A, which includes a UV source in accordance with an embodiment.

One or more walls 1102a-f may support components which allow walls 1102a-f, as well as items within a space defined by walls 1102a-f, to be sanitized, disinfected, and/or cleaned. For example, UV sources such as UV light bulbs and/or UV light emitting diodes (LEDs) may be supported on one or more walls 1102a-f. As shown in FIG. 11B, back wall 1176 may support a UV source 1176. In one embodiment, UV source 1176 may be arranged to emit UV waves that may inactivate contaminants such as viruses upon the waves contacting the contaminants. UV source 1176 may be powered by a dedicated batter, as for example a battery that powers substantially only UV source 1176, or UV source 1176 may be powered by a power system of the vehicle if which compartment 1102 is a part.

Figure 11C:
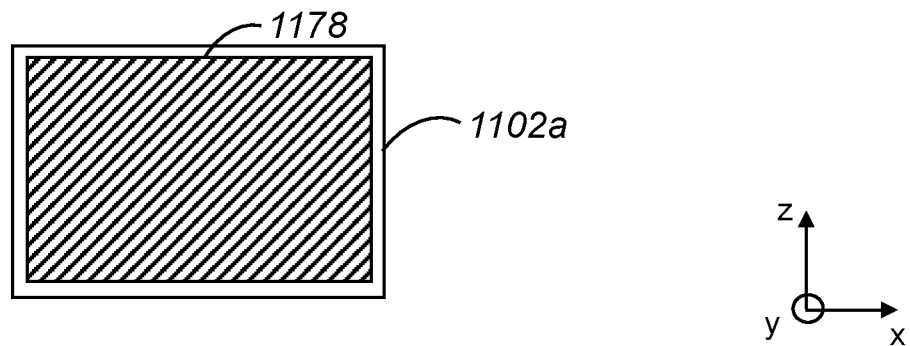
FIG. 11C is a diagrammatic representation of a wall of a compartment, e.g., compartment 1102 of FIG. 11A, which includes a reflective surface such as a mirror surface in accordance with an embodiment.

Walls 1102a-f may include reflective surfaces, e.g., mirror surfaces or foil surfaces, which facilitate the use of UV sources such as UV source 1176. Waves emitted by UV source 1176 may contact reflective surfaces and reflect off, thereby enable waves to essentially cover additional space. Front wall 1102a, as shown in FIG. 11C, includes a reflective surface 1178. Reflective surface 1178, as shown, is located on a side of front wall 1102a that faces an interior of compartment 1102, and is arranged to reflect UV waves emitted by UV source 1176.

Figure 11D:
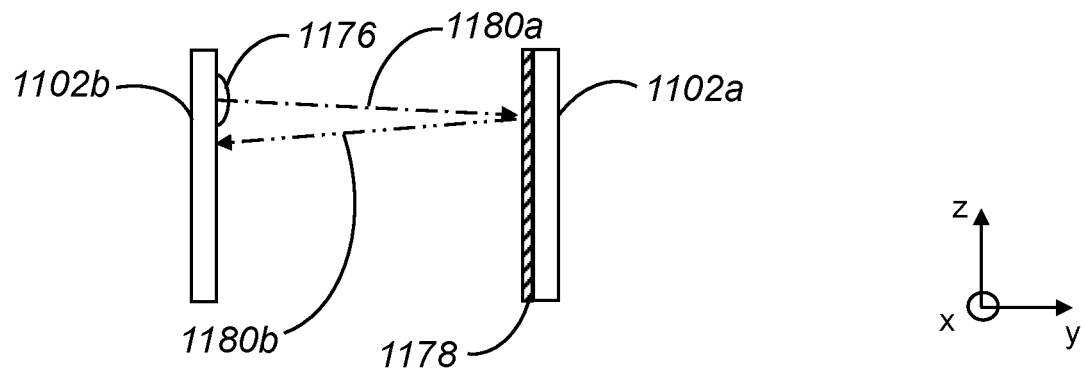
FIG. 11D is a diagrammatic side-view cross-sectional representation of walls of a compartment, e.g., compartment 1102 of FIG. 11A, which are configured to allow waves from a UV source, e.g., UV source 1176 of FIG. 11B, to reflect off of a mirror surface, e.g., mirror surface, in accordance with an embodiment.

FIG. 11D is a diagrammatic side-view cross-sectional representation of walls 1102a, 1102b in accordance with an embodiment. When UV source 1176 is activated, a beam 1180a may be emitted by or otherwise generated by UV source 1176. Beam 1180a may traverse the space within compartment 1108 and reflect off of reflective surface 1178 as reflected beam 1180b, and reflected beam 1180b may be directed towards wall 1102b. In one embodiment, wall 1102b may also include a reflective surface (not shown). As beam 1180a and reflected beam 1180b pass within compartment 1102, beam 1180a and beam 1180b may effectively sanitize, disinfect, and/or clean compartment 1102 by causing contaminants such as viruses to become inactivated. It should be appreciated that UV source 1176 may generally emit multiple beams, and that the wavelength of the beams may vary widely. In one embodiment, reflective surface 1178 may be a shield which may hamper or otherwise prevent the passage of beam 1180a through wall 1102a. For example, reflective surface 1178 may be formed from aluminum, and may reduce the leakage of UV waves through wall 1102a while reflecting waves or beams within compartment 1102.

Figure 11E:
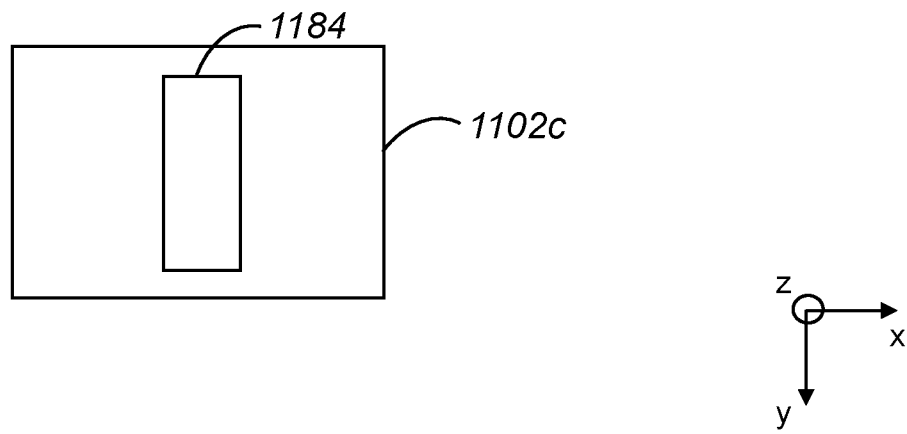
FIG. 11E is a diagrammatic representation of a wall of a compartment, e.g., compartment 1102 of FIG. 11A, which includes a dispenser configured to dispense a cleaning substance in accordance with an embodiment.

Compartment 1102 may be arranged to be sanitized, disinfected, and/or cleaned using material that may be dispensed or dispersed within compartment 1102. Such material may be a cleaning solution. In one embodiment, a dispenser of material may be supported on ceiling 1102c to facilitate the distribution of the material throughout compartment 1102. FIG. 11E is a diagrammatic representation of ceiling 1102c which supports a dispenser configured to dispense a cleaning substance in accordance with an embodiment. A dispenser 1184 may be connected to a reservoir (not shown) that holds a cleaning substance, and may be supported on a surface of ceiling 1102c that faces into an interior volume of compartment 1102. Dispenser 1187, when activated, may cause the cleaning substance to be dispensed within compartment 1102. Dispenser 1187 may include at least one nozzle, as for example a sprinkler nozzle, a mister nozzle, and/or a hose nozzle. Dispenser 1187 may also be configured to include a drip distribution system, an/or a gas distribution system, as for example when a cleaning substance is gas, steam, and/or a vapor.

Figure 11F:
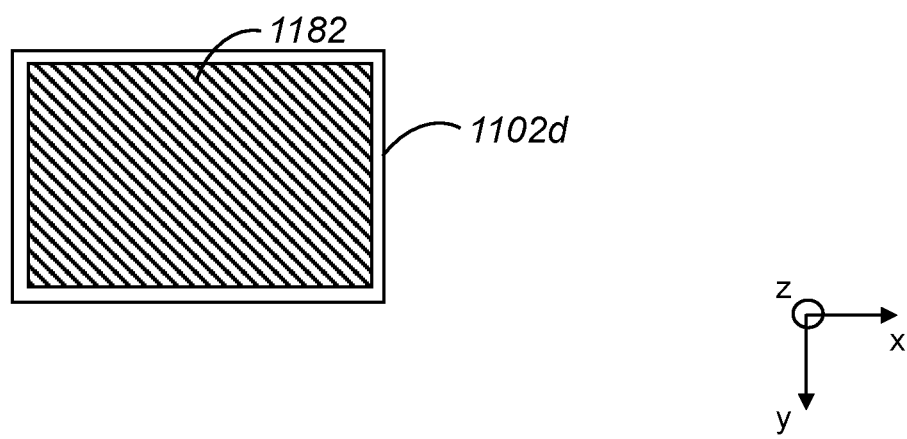
FIG. 11F is a diagrammatic representation of a wall of a compartment, e.g., compartment 1102 of FIG. 11A, which includes a sterilizing film in accordance with an embodiment.

As previously mentioned, surfaces of walls 1102a-f may be covered with material which facilitates the sanitizing, disinfecting, and/or cleaning of compartment 1102. The surfaces of walls 1102a-f on which material may be adhered or otherwise applied are generally surfaces that may become contaminated, e.g., surfaces of walls 1102a-f that substantially define a space within compartment 1102. One or more walls 1102a-f may have reflective surfaces such as mirrored surfaces. It should be appreciated that other materials may be applied to walls 1102a-f in addition to, or in lieu of, reflective materials. By way of example, a sterilizing film may be applied to one or more walls 1102a-f FIG. 11F is a diagrammatic representation of bottom wall 1102d which includes a sterilizing film such as an anti-microbial film in accordance with an embodiment. A sterilizing film 1182 may be applied or otherwise coupled to an interior side of bottom surface 1102d, or a side of bottom surface 1102d that is substantially on an inside of compartment 1102. Bottom surface 1102d may generally be a surface on which goods transported within compartment 1102 are placed. Sterilizing film 1182 may substantially prevent contaminants such as bacteria from remaining active or alive. In one embodiment, sterilizing film 1182 may be formed from materials including, but not limited to including, copper and/or silver. Sterilizing film 1182 may be formed as antimicrobial pads using copper-infused and/or silver-infuse materials. While sterilizing film 1182 may generally be formed as a sheet or a roll of film, it should be appreciated that sterilizing film 1182 is not limited to being formed as a sheet or a roll of film, e.g., sterilizing film 1182 may be a sprayed on film. In one embodiment, sterilizing film 1182 may effectively be impregnated onto bottom surface 1102d or integrally formed with bottom wall 1102d.

Figure 12:
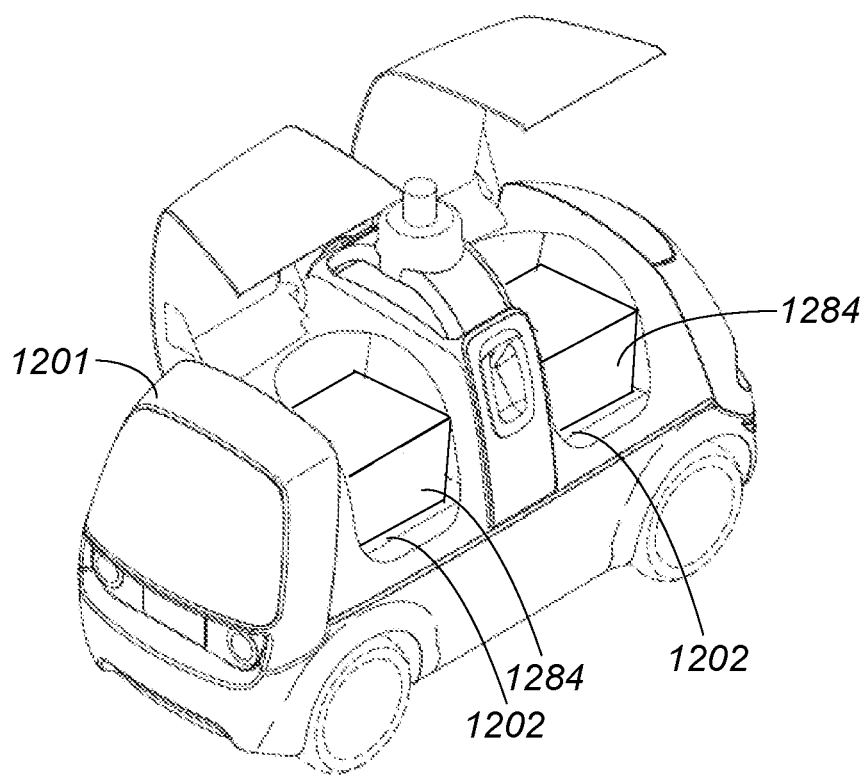
FIG. 12 is a diagrammatic representation of a vehicle which includes compartments configured to accommodate compartment inserts in accordance with an embodiment.

While a compartment such as compartment 1102 of FIGS. 11A-F may be provided with systems which enable compartment 1102 to be sanitized, disinfected, and/or cleaned, some compartments may support the use of compartment inserts. Compartment inserts may be modules which enable compartments to be configured. FIG. 12 is a diagrammatic representation of a vehicle which includes compartments configured to accommodate compartment inserts in accordance with an embodiment. A vehicle 1201, which may be an autonomous vehicle, includes compartments 1202. Each compartment 1202 may accommodate a compartment insert 1284. Compartment inserts 1284 may vary widely, and may provide capabilities including, but not limited to including, cooling, and heating. The use of compartment inserts 1284 allows vehicle 1201 to effectively be configured for particular purposes.

Compartment inserts 1284 may, in one embodiment, be configured to provide sanitizing, disinfecting, and/or cleaning capabilities. That is, compartment inserts 1284 may be arranged to sanitize, disinfect, and/or clean their interiors and/or items carried within compartment inserts 1284. The use of compartments inserts 1284 to provide sanitizing, disinfection, and/or cleaning capabilities allows such capabilities to effectively be removed from, and added to, vehicle 1201 as desired. In other words, compartment inserts 1284 generally allow vehicle 1201 to be configurable.

Figure 13A:
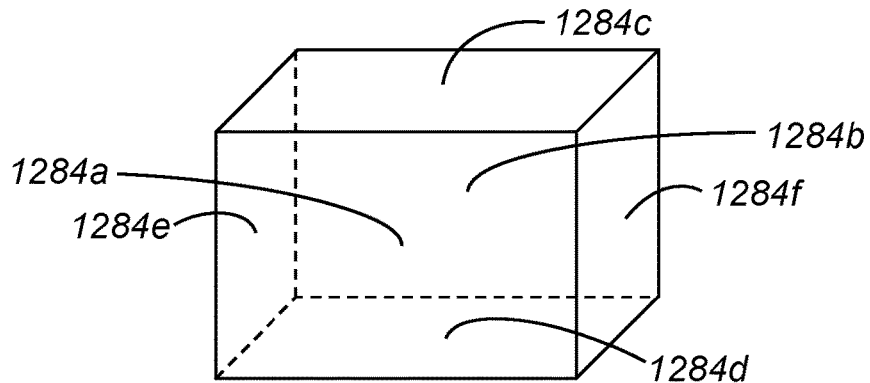
FIG. 13A is a diagrammatic representation of a compartment insert, e.g., compartment insert 1284 of FIG. 12, in accordance with an embodiment.
Figure 13A:
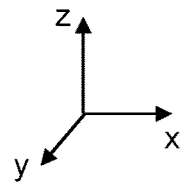

FIG. 13A is a diagrammatic representation of a compartment insert, e.g., compartment insert 1284 of FIG. 12, in accordance with an embodiment. Compartment insert 1284 includes walls 1284*a-f*. Walls 1284*a-f* of compartment insert include a front wall 1284*a*, a back wall 1284*b*, a top wall or ceiling 1284*c*, a bottom wall or base 1284*d*, a first side wall 1284*e*, and a second side wall 1284*f*. Front wall 1284*a* may include a door or cover that may be opened and closed, and/or unlocked and locked, to enable the interior volume of compartment insert 1284 to be accessed.

Similar to the walls discussed above with respect to FIGS. 11A-F, one or more walls 1284*a-f* may support components which allow walls 1284*a-f*, as well as items within a space defined by walls 1284*a-f*, to be sanitized, disinfected, and/or cleaned. That is, walls 1284*a-f* may include, but are not limited to including, components arranged to provide UV disinfecting and cleaning solutions. In one embodiment, walls 1284*a-f* may be configured to support a heat source arranged to provide heat within compartment insert 1284.

Compartment insert 1284 may be configured to interface with a vehicle through a compartment, e.g., vehicle 1201 and compartment 1202 of FIG. 12, in which compartment insert 1284 is inserted. For example, compartment insert 1284 may be configured to interface with a vehicle to draw power to enable sanitizing, disinfecting, and/or cleaning systems to be activated.

Figure 13B:
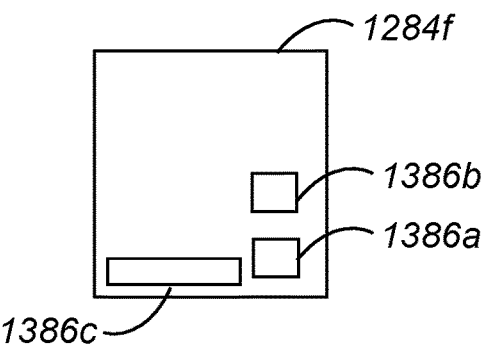
FIG. 13B is a diagrammatic representation of a wall of a compartment insert, e.g., compartment insert 1284 of FIGS. 12 and 13A, which includes a power interface, a communications interface, and a mechanical interface in accordance with an embodiment.
Figure 13B:
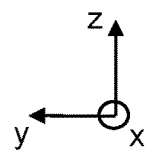
Figure 13C:
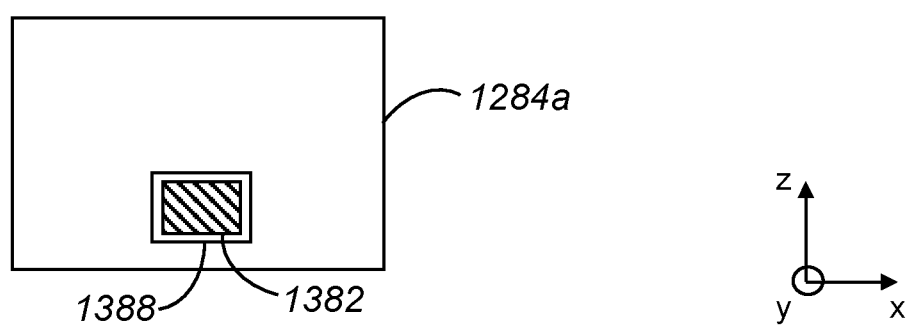
FIG. 13C is a diagrammatic representation of a wall of a compartment insert, e.g., compartment insert 1284 of FIGS. 12 and 13A, which includes a door opening interface in accordance with an embodiment.

In one embodiment, compartment insert 1284 is configured to communicate with a vehicle. That is, compartment insert 1284 may be a "smart" compartment insert. The interface between compartment insert 1284 and a compartment such as compartment 1202 of FIG. 12 may be a mechanical interface, a power interface, and/or a communications interface. FIG. 13B is a diagrammatic representation of side wall 1284*f* which includes a power interface, a communications interface, and a mechanical interface in accordance with an embodiment. Side wall 1284*f* may include a power connector 1386*a* which is configured to draw power from a vehicle. Such power may be electrical power or battery power. It should be appreciated that if compartment insert 1284 includes a dedicated battery, power connector 1286*a* may be optional. Side wall 1284*f* also includes a communications interface 1386*b*. Communications interface 1386*b* may be configured to support wired and/or wireless communications. For example, communications interface 1386*b* may be arranged to substantially connect to a communication bus on a vehicle, or communications interface 1386*b* may be arranged to engage in communications such as Bluetooth communications, Wi-Fi communications, LTE communications, and/or wireless 3G/4G/5G communications. Side wall 1284*f* also includes a mechanical interface 1386*c* which is arranged to enable compartment insert 1284 to be mechanically coupled to a compartment such as compartment 1202 of FIG. 12B.

In one embodiment, areas of compartment insert 1284 may be considered to be "high touch" areas, or areas which an individual may be relatively likely to touch or otherwise physically contact. For example, when compartment insert wall 1284*a* is door, compartment insert wall 1284*a* may include a door handle which an individual who either places an item in compartment insert 1284 or removes an item from compartment insert 1284 may touch. As shown in FIG. 133, a door opening interface 1388, e.g., a door handle, may be included as a part of front compartment insert wall 1284*a*. Door opening interface 1388 may be a mechanism that is coupled to front compartment insert wall 1284*a*, or may be an integrated portion of front compartment insert wall 1284*a*. For a relatively high touch area such as door opening interface 1388, a sterilizing material or film 1382 may be applied to substantially increase protection from contaminants for anyone who may touch door opening interface 1388.

Figure 14A:
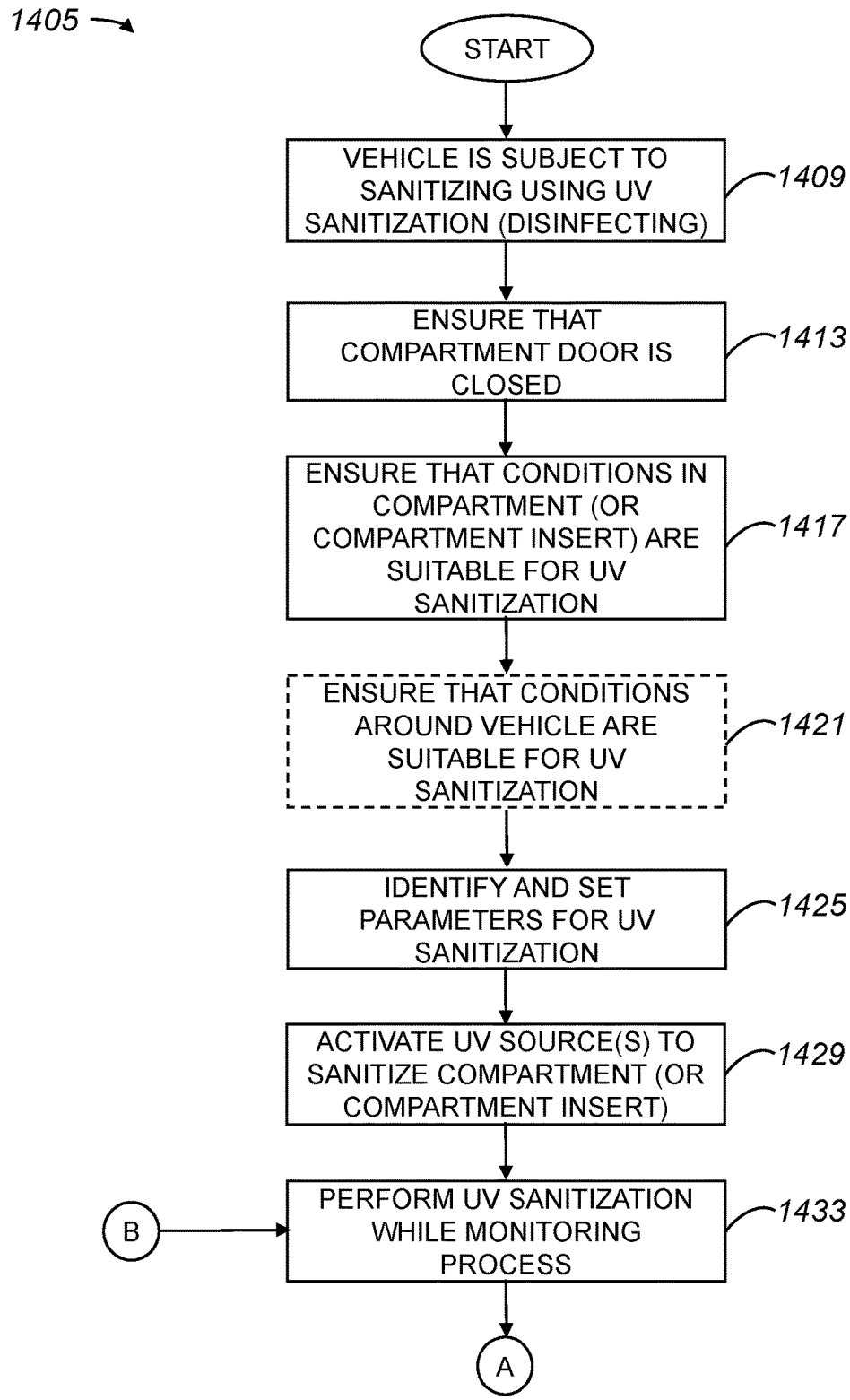
FIGS. 14A and 14B are a process flow diagram which illustrates a method of using UV sanitization to sanitize a compartment of a vehicle or a compartment insert within a compartment of a vehicle in accordance with an embodiment.
Figure 14B:
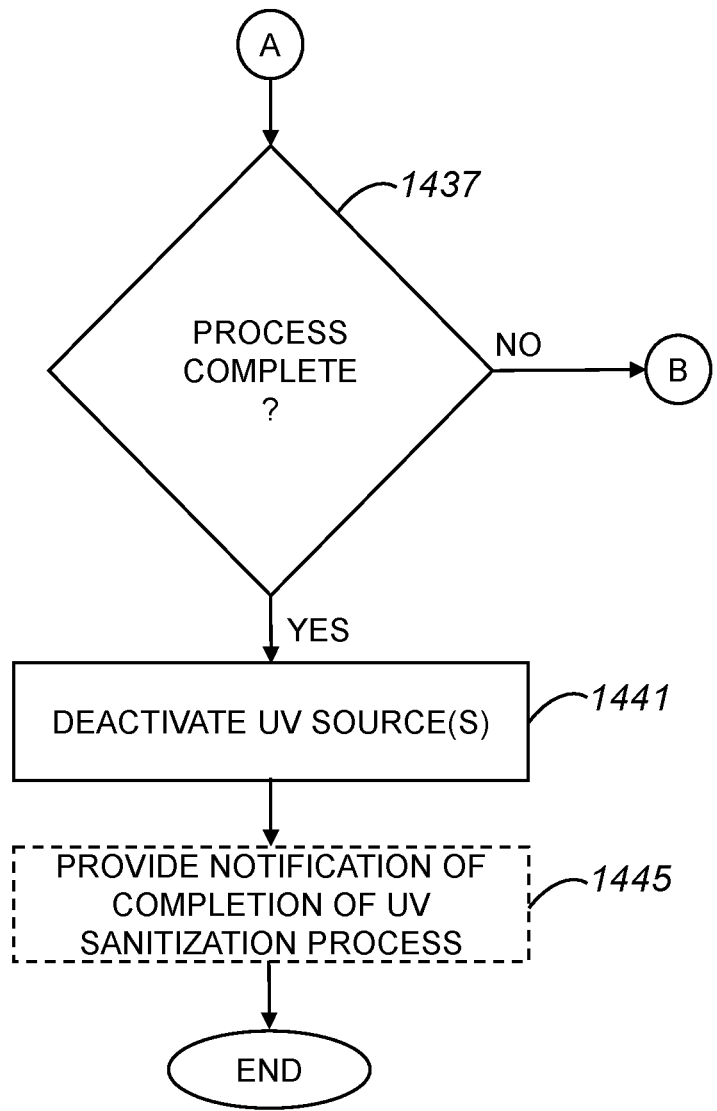

As mentioned above, a UV sanitization or disinfecting process may utilize one or more UV sources or UV light sources. Such UV sources may be located within a compartment of a vehicle, or may be located within a compartment insert which may be placed in the compartment of the vehicle. FIGS. 14A and 14B are a process flow diagram which illustrates a method of using UV sanitization to sanitize a compartment of a vehicle or a compartment insert within a compartment of a vehicle in accordance with an embodiment. A method 1405 of providing UV sanitization for a compartment or a compartment insert begins at a step 1409 in which a vehicle is identified as being subject to sanitizing, or a sanitization process using UV sanitization. Identifying such a vehicle may include, but is not limited to including, determining that a retailer or seller has requested UV sanitization, determining that a customer has requested UV sanitization, determining that a level of contamination or a pathogen level in a compartment or compartment insert is at least at a threshold for performing UV sanitization, determining that a schedule indicates that the vehicle is due for UV sanitization, and/or determining that the vehicle is to undergo UV sanitization prior to or after each delivery.

Once the vehicle is identified as being subject to a UV sanitization process, in a step 1413, it is effectively ensured that a compartment door, e.g., a door on a compartment and/or a door on a compartment insert, is closed or otherwise secured. As UV waves may have an adverse effect on humans, ensuring that a compartment door is closed reduces the likelihood that any human in the vicinity of the vehicle may be affected. In one embodiment, the compartment door may be shielded to provide additional protection for humans who may be in the vicinity of the vehicle when a UV sanitization process occurs.

From step 1413, process flow moves to a step 1417 in which it is substantially ensured that conditions in the compartment, or the compartment insert, are appropriate for UV sanitization to occur. In one embodiment, a compartment or compartment insert may be determined to not be in condition for UV sanitization if there is steam or condensation in the compartment. It should be appreciated that if it is ascertained that a compartment or compartment insert is not in condition for UV sanitization, mitigation measures may be taken to essentially place the compartment or compartment insert in condition for UV sanitization. By way of example, if a compartment has steam or condensation, the steam or condensation may be removed from the compartment in order to render the compartment as being in condition for UV sanitization to occur.

In an optional step 1421, it may be ensured that conditions around the vehicle are suitable for UV sanitization. Ensuring that conditions around the vehicle are suitable for UV sanitization may generally include, but are not limited to including, ensuring that there are no humans within a particular range of the vehicle, and/or ensuring that there are no objects in the vicinity of the vehicle which may adversely affect a UV sanitization process. If the vehicle detects a human within a particular range of the vehicle, the vehicle may broadcast a message that may be obtained by the human and/or the vehicle may wait for the human to move out of the particular range in order to ensure conditions that are suitable for UV sanitization.

From step 1417 or from optional step 1421, process flow proceeds to a step 1425 in which parameters for UV sanitization are identified and set. The parameters for UV sanitization may be default parameters associated with the vehicle. Alternatively, the parameters may be set or otherwise specified by a seller and/or a customer. In one embodiment, the parameters may be set based upon measured contaminant, e.g., pathogen, levels within the compartment or compartment insert. The parameters may include, but are not limited to including, a number of UV sources to activate, locations of UV sources to activate, a duration or length of time for a UV sanitization process, a desired level of sanitization or cleanliness, and/or a desired intensity or wavelength for the UV sources. A desired level of sanitization or cleanliness may be an amount or a percentage of a particular contaminant detected in a compartment. A desired level of sanitization may vary depending upon factors including, but not limited to including, the growth rate of a pathogen. The desired level of sanitization may be specified as a percentage, e.g., less than approximately 0.1 percent, of a pathogen detected that may substantially prevent an exponential growth rate of pathogens from reaching a particular threshold in a particular amount of time, e.g., a pathogen may occupy less than approximately twenty five percent per cubic meter within approximately two hours. In one embodiment, parameters may be obtained from a seller or a customer using a smartphone application or an online application which may be used to communicate with the vehicle.

After the parameters are identified and set in step 1425, at least one UV source is activated to sanitize the compartment or the compartment insert. Activating at least one UV source generally includes activating the at least one UV source based upon parameters identified and set in step 1429. A UV source may be any suitable UV source, as for an example a UV light source such as a short-wavelength UV lamp or a UV LED, e.g., a UVC LED. Such as UV source may emit UV waves in a range of between approximately 200 nm and approximately 500 nm, e.g., between approximately 222 nm and approximately 254 nm.

In a step 1433, a UV sanitization is performed using the at least one activated UV source. As the UV sanitization is performed, the process may be monitored. Monitoring the process may include, but is not limited to including, obtaining sensor readings to monitor conditions within a compartment or compartment insert. determining whether the UV waves are being generated, and/or determining whether the UV sanitization process has been disrupted.

A determination is made in a step 1437 as to whether UV sanitization is complete. That is, it is determined whether UV sanitization has either resulted in a compartment or compartment insert being sanitized. In one embodiment, such a determination may include determining whether UV sanitization has been prematurely terminated, as for example by a loss of power or an opening of a compartment door.

If the determination in step 1437 is that UV sanitization is not complete, process flow returns to step 1433 in which UV sanitization continues. Alternatively, if the determination in step 1437 is that UV sanitization is complete, then in a step 1441, at least one UV source is deactivated. Once the at least one UV source is deactivated, notification of the completion of UV sanitization may be optionally provided in a step 1445. That is, in optional step 1445, the vehicle may notify a fleet management system, a seller, and/or a customer that UV sanitization is completed. Upon deactivating any activated UV sources, and optionally providing notification of the completion of UV sanitization, the method of providing UV sanitization for a compartment or a compartment insert is completed.

Within a compartment or a compartment insert or, more generally, within a space onboard a vehicle that is to be subject to a UV sanitizing process, one or more UV sources may be mounted in various configurations. For example, one or more UV sources may be mounted to each wall of a compartment. The configuration or orientation of the UV sources may be selected to optimize the illumination on specific locations of interest within a compartment. The UV sources may be mounted using mechanical components, adhesives, and/or magnets. Power to the UV sources may be provided by one or more dedicated batteries, or from a general power source onboard a vehicle.

In one embodiment, a compartment may include approximately five UV sources, with each UV source mounted on an interior wall of the compartment with the exception of the wall that includes a door to the compartment. The five UV sources may each be an array of UV LEDs, or may be five UV light bulbs. It should be appreciated that additional UV sources may be mounted on interior walls of the compartment, e.g., on edges of the compartment such that UV beams may be relatively evenly distributed within the compartment. In general, the number of UV sources mounted within a compartment may vary depending upon the geometry of the compartment. That is, the number of UV sources is not limited to being five, and may include fewer than or more than five UV sources.

In general, the number of UV sources and the geometry associated with mounting the UV sources may be selected to substantially ensure that the totality of UV sources have lines of sight or reflective lines of sight to substantially all surfaces that are to be sanitized. In one embodiment, in order to provide a customer with a substantially clear line of sight to his or her goods in a compartment once the compartment is open, UV sources may be positioned on a top interior surface of the compartment and on an interior door surfaces.

Figure 15:
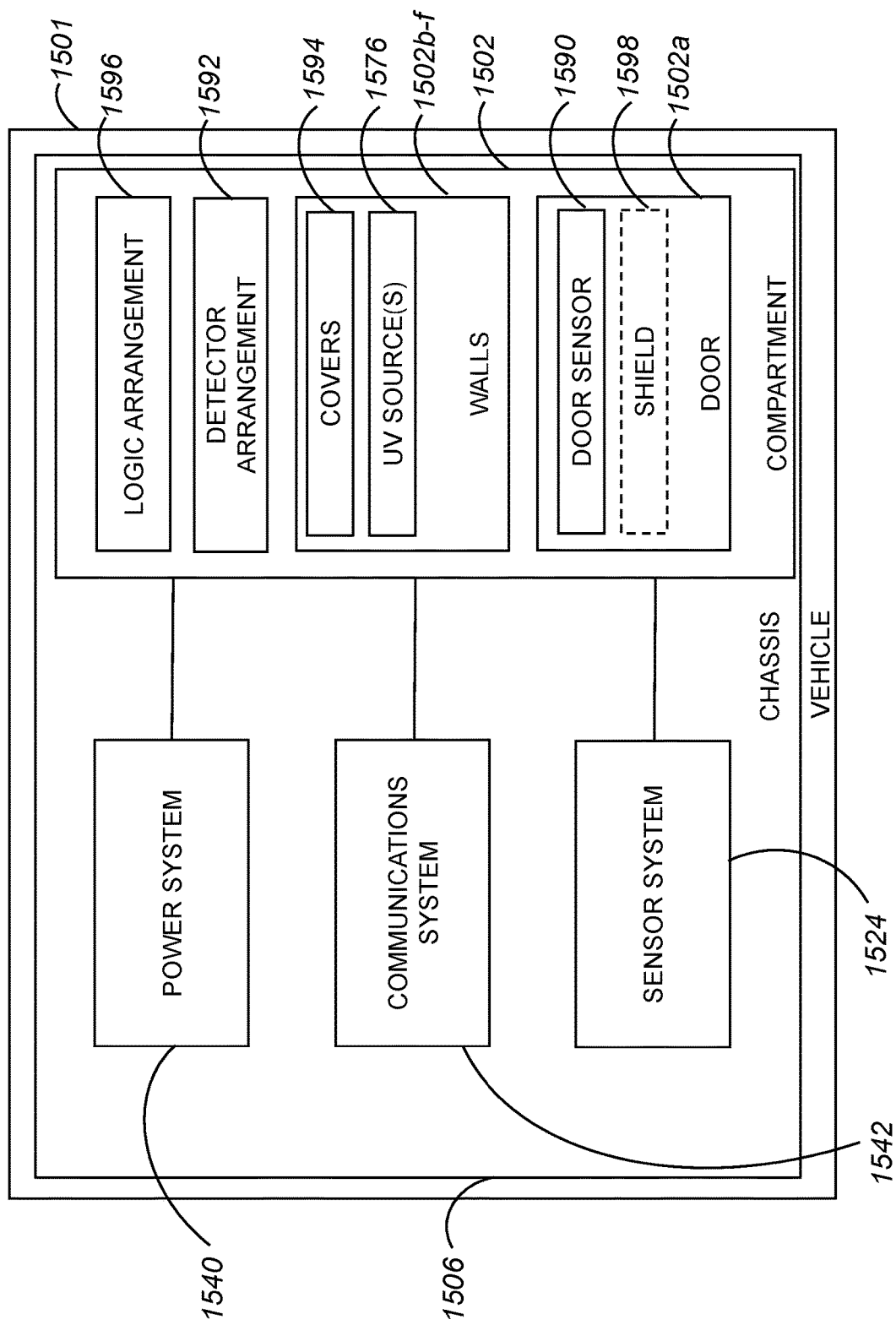
FIG. 15 is a block diagram representation of a vehicle that is configured to provide UV sanitization within a compartment of the vehicle in accordance with an embodiment.

FIG. 15 is a block diagram representation of a vehicle that is configured to provide UV sanitization within a compartment of the vehicle in accordance with an embodiment. A vehicle 1501, which may be an autonomous delivery vehicle or an autonomous passenger vehicle, includes a compartment 1502. Vehicle 1501 also includes systems such as those shown in FIG. 3, such as a power system 1540, a communications system 1542, and a sensor system 1524. Power system 1540, communication system 1542, and sensor system 1524 may be coupled to compartment 1502 and/or components within, or otherwise associated with, compartment 1502. In general, vehicle 1501 includes a chassis or a frame 1506, and compartment 1502, power system 1540, communications system 1542, and sensor system 1524 may be carried on, or supported on, chassis 1506.

Compartment 1502 includes a front wall or a door 1502*a*, as well as approximately five additional walls 1502*b-f* or more. In general, a storage space or volume within compartment 1502 is substantially defined by door 1502*a* and walls 1502*b-f* One or more of door 1502*a* and walls 1502*b-f* may include reflective surfaces.

Door 1502*a* may include a door sensor 1590 which may be configured to determine when door 1502*a* is in an open position or in a closed position. It should be appreciated that when door 1502a is in an open position, UV sanitization may not be initialized. UV sanitization may occur when door sensor 1590 detects that door 1502a is in a closed position. Door sensor 1590 may be included as a part of sensor system 1524 or may be a part of a UV sanitization system. In one embodiment, door 1502a includes an optional shield 1598.

One or more UV sources 1576 are coupled to, or are integrated with, walls 1502b-f In one embodiment, each wall 1502b-f may have at least one UV source 1576 mounted thereon. UV sources 1576 may include, but are not limited to including, UV LEDs, arrays of UV LEDs, and/or UV light bulbs. UV waves generated by UV sources 1576 may reflect off of door 1502a and walls 1502b-f, e.g., off of reflective surfaces of door 1502a and walls 1502b-f Optional shield 1598 may substantially prevent UV wave from passing through door 1502a.

UV sources 1576 may have covers 1594, e.g., protective covers, which protect UV sources 1576 from damage. By way of example, covers 1594 may be arranged over or on UV sources 1576 to protect UV sources from chemicals, liquids, heat, moisture, steam, and/or condensation. In general, covers 1594 may be formed from materials through which UV waves such as UV light waves may pass. When compartment 1502 is configured to be disinfected or cleaned using heat, covers 1594 may protect UV sources 1576 from steam or condensation that results from the heat.

Compartment 1502 includes a detector arrangement 1592 which may detect conditions within compartment 1502. For example, detector arrangement 1592 may include a pathogen detection sensor configured to detect pathogen levels within compartment 1502. The pathogen detection sensor may measure a pathogen level in compartment 1502 at substantially any time, as for example at the onset of UV sanitization, during UV sanitization, and after UV sanitization. Detector arrangement 1592 may also include, but is not limited to including, a moisture level sensor, a thermometer, a humidity sensor, a weight sensor, a microphone, and/or a camera.

Detector arrangement 1592 is arranged to communicate with logic arrangement 1596 to provide information which may be used by logic arrangement 1592 to determine parameters to use for UV sanitization. For example, if a pathogen detection sensor detects a particular pathogen level within compartment 1502, logic arrangement 1596 may determine a duration for UV sanitization which may be suitable for reducing the pathogen level to an acceptable level. It should be appreciated that while logic arrangement 1596 is shown as being onboard vehicle 1501, logic arrangement 1596 may be distributed such that some logic is onboard vehicle 1501 while other logic is substantially remote, as for example hosted on an external server. Logic arrangement 1596, which may include hardware and/or software logic, may also use data from door sensor 1590 to determine when to initiate UV sanitization and when to terminate UV sanitization. By way of example, when door 1502a is detected by door sensor 1590 to be closed, logic arrangement 1596 may initiate UV sanitization. On the other hand, when door 1502a is detected to be open while UV sanitization is in progress, logic arrangement 1596 may terminate UV sanitization.

In general, logic arrangement 1596 may use information or data provided by sensor system 1524 with respect to UV sanitization. For example, cameras included in sensor system 1524 may provide data which enables logic arrangement 1596 to determine whether there are humans present near vehicle 1501, and to cause any nearby humans to be warned to move away from vehicle 1501 prior to initiating UV sanitization. Logic arrangement 1596 may utilize communications system 1542 to communicate with humans near a vehicle.

While UV sources 1576 may include dedicated power sources, e.g., batteries, UV sources 1576 may instead draw power, e.g., electricity, from power system 1540. It should be understood that logic arrangement 1596, detector arrangement 1592, and door sensor 1590 may obtain power from power system 1540.

In one embodiment, door 1502a, walls 1520b-f, detector arrangement 1592, and logic arrangement 1596 may be part of a compartment insert carried within compartment 1502. As such, UV sanitization may be provided by a compartment insert that is located in compartment 1502.

Although only a few embodiments have been described in this disclosure, it should be understood that the disclosure may be embodied in many other specific forms without departing from the spirit or the scope of the present disclosure. By way of example, as described above with respect to FIG. 4, an item placed in a compartment of an autonomous vehicle may be disinfected, sanitized, sterilized, purified, and/or otherwise cleaned either before, during, and/or at delivery. In lieu of disinfecting, sanitizing, sterilizing, purifying, and/or otherwise cleaning an item in the context of delivering the item, an autonomous vehicle may be used to decontaminate an item without delivering the item. That is, a compartment of an autonomous vehicle may serve as an autoclave or sterilization compartment substantially on demand. In one embodiment, a customer may summon an autonomous vehicle to a customer location purely to allow the customer to utilize a sterilization compartment of the autonomous vehicle to sterilize possessions of the customer.

It should be appreciated that methods described in terms of sanitizing and disinfecting surfaces may generally be associated with cleaning surfaces. That is, while sanitizing and disinfecting may refer to cleaning, cleaning may also refer to sanitizing and disinfecting without departing from the spirit of the scope of the disclosure. In addition, sanitizing, disinfecting, and/or cleaning surfaces may also generally refer to cleansing, washing, purifying, decontaminating, fumigating, depolluting, and/or sterilizing surfaces.

A vehicle with a compartment that includes the ability to disinfect, sanitize, sterilize, and/or clean items placed therein may be used for the capabilities of the compartment. For instance, a vehicle may be used at a field hospital or at a remote, e.g., outdoor, location at which medical procedures are performed to provide the ability to disinfect items such as medical tools. Similarly, a vehicle that carries components that may administer and/or run medical tests may be used at a field hospital or at a remote location at which medical procedures.

While the methods and systems described above have generally been described in the context of a shelter-in-place order or a stay-at-home order, it should be understood that the methods and systems are not limited to being utilized during a crisis such as a pandemic. By way of example, a customer may have the ability to request that his or her delivered items be disinfected or otherwise cleaned even when there is no pandemic.

The ability to disinfect or otherwise clean items delivered or, more generally, transported by an autonomous vehicle is not limited to being used when there is a relatively high possibility that the items may be contaminated, e.g., with a virus such as COVID-19. In other words, delivered or transported items may be disinfected or otherwise cleaned whenever the items are onboard an autonomous vehicle with disinfecting or cleaning capabilities. A customer may request disinfecting or cleaning of an ordered item, or the disinfecting or cleaning may be substantially automatic once the customer orders the item and the item is placed in a compartment of an autonomous delivery vehicle.

An autonomous vehicle may be used, in one embodiment, as a monitoring or surveillance vehicle when a shelter-in-place or a stay-at-home or deter is in effect. By way of example, an autonomous vehicle may have an onboard heat sensor that may be used to scan a location such as a house to determine if there are areas of heat in the house that indicate that there are occupants in the house. Such a heat sensor may also be used as a diagnostic tool to determine whether any person in the vicinity of the heat sensor has an elevated temperature. In one embodiment, sensors used to allow a vehicle to operate autonomously may be leveraged for monitoring purposes such as public health monitoring purposes.

In some instances, it may be necessary to provide additional power capabilities on an autonomous vehicle. For example, it may be desirable to provide a dedicated power source to power sanitizing/cleaning system 344 of FIG. 3. Additional power may be provided by a power supply such as a battery pack located in a compartment of the autonomous vehicle.

When sanitizing/cleaning system 344 of FIG. 3 includes a heat source, it may not be possible to clean all items using the heat source. Some items may, for instance, not be well-suited to a cleaning process that involves the application of heat. Items that are not suited to withstand the application of heat may be delivered using vehicles which utilize other cleaning mechanisms. It should be understood, however, that if it is not possible to clean an item using heat and there are no available vehicles that have other cleaning mechanisms, a recipient of a delivery of the item may be warned that the item has not been cleaned.

The ability for a customer to access a compartment of a delivery vehicle in a contactless manner has been described as being achieved in some cases through communications with a fleet management system. In one embodiment, when a delivery vehicle is controlled via teleoperations, a remote operator may open a door on a compartment of the vehicle when the remote operator sees that a customer is ready to accept a delivery without departing from the spirit or the scope of the disclosure.

An autonomous vehicle may be arranged to enable its surroundings, or a person or object positioned in the vicinity of the autonomous vehicle, to be substantially sprayed or showered with a substance such as a disinfectant. That is, a nozzle or sprinkler system may be installed on an autonomous vehicle to dispense a disinfectant or other fluid such as water or insect repellant. For example, to ensure that a person is not covered with a pathogen, a disinfectant may be misted over the person. The capability to dispense a fluid from an autonomous vehicle into its surroundings may be extended to dispense other fluid such as an air freshener, a perfume, and a cologne. To facilitate the distribution of fluid, a system similar to system 344*b*, as discussed above with reference to FIG. 7, may be used. For instance, system 344*b* of FIG. 7 may essentially be modified such that a fluid distribution mechanism may substantially spray a person or object in the vicinity of a vehicle, rather than the vehicle.

As mentioned above, a disinfecting compartment of a vehicle may be used as an autoclave to provide disinfecting capabilities. Such disinfecting capabilities may be arranged to disinfect, for example, used medical-grade face masks to allow the masks to be safely reused.

In one embodiment, after disinfecting or cleaning occurs, a pathogen detection sensor may determine that a pathogen level remains too high, e.g., is greater than approximately 0.1%. When a pathogen level is over a threshold after a disinfecting process such as a UV sanitization process is completed the disinfecting process may effectively be repeated until an acceptable pathogen level is achieved. Alternatively, when a pathogen level remains above a threshold level after one type of disinfecting or cleaning process is completed, a different disinfecting or cleaning process may be initialized.

Sterilizing materials or films have been described above as being applied to high touch areas of a vehicle, e.g., a handle of a compartment or a handle of a compartment insert. Sterilizing materials such as antimicrobial materials are not limited to being applied to high touch areas of a vehicle or to surfaces associated with compartments or compartment inserts. For instance, sterilizing materials or films may be applied to external surfaces of a vehicle.

A sanitization process may be performed as a vehicle travels, e.g., from a seller to a buyer or from a retailer to a customer. When a sanitization process is performed while a vehicle is driving to a destination, the sanitization process may be timed to be completed when the vehicle arrives at the destination. Alternatively, a sanitization process may be substantially timed such that when a vehicle that is delivering an item reaches an intended destination, the item is sanitized and in condition to be removed from the vehicle. By way of example, if the item is sanitized using heat, a heat sanitization process may be timed to be completed in time for the item to reach an ambient temperature when the vehicle arrives at an intended destination. In one embodiment, when a sanitization process is performed to sanitize an empty compartment of a vehicle while the vehicle travels, the sanitization process may be timed such that when the vehicle reaches an intended destination, the compartment is at an ambient temperature and/or is not wet from steam, condensation, and/or the application of sanitizing chemicals.

In general, while a vehicle may be substantially outfitted with more than one sanitization system arranged to sanitize a compartment, some vehicles may include a single sanitization system. When a vehicle includes a single sanitization system, that sanitization system may be selected based upon a percentage of situations or scenarios in which the sanitization system provides effective sanitization. It should be appreciated that operational methods may be implemented to substantially work around a situation in which the selected sanitization system may be less effective than desired.

Materials from which a compartment is formed, e.g., materials from which a compartment door is formed, may be arranged to be antimicrobial. Similarly, materials from which a compartment insert is formed may also be antimicrobial. By way of example, a compartment door and/or a compartment insert may be formed from a material that includes copper and/or silver.

An autonomous vehicle has generally been described as a land vehicle, or a vehicle that is arranged to be propelled or conveyed on land. It should be appreciated that in some embodiments, an autonomous vehicle may be configured for water travel, hover travel, and or/air travel without departing from the spirit or the scope of the present disclosure. Further, while an autonomous vehicle has generally been described as a delivery vehicle, the methods described above may be applied to an autonomous vehicle, or substantially any other vehicle, that is arranged to transport passengers.

The embodiments may be implemented as hardware, firmware, and/or software logic embodied in a tangible, i.e., non-transitory, medium that, when executed, is operable to perform the various methods and processes described above. That is, the logic may be embodied as physical arrangements, modules, or components. For example, the systems of an autonomous vehicle, as described above with respect to FIG. 3, may include hardware, firmware, and/or software embodied on a tangible medium. A tangible medium may be substantially any computer-readable medium that is capable of storing logic or computer program code which may be executed, e.g., by a processor or an overall computing system, to perform methods and functions associated with the embodiments. Such computer-readable mediums may include, but are not limited to including, physical storage and/or memory devices. Executable logic may include, but is not limited to including, code devices, computer program code, and/or executable computer commands or instructions.

It should be appreciated that a computer-readable medium, or a machine-readable medium, may include transitory embodiments and/or non-transitory embodiments, e.g., signals or signals embodied in carrier waves. That is, a computer-readable medium may be associated with non-transitory tangible media and transitory propagating signals.

The steps associated with the methods of the present disclosure may vary widely. Steps may be added, removed, altered, combined, and reordered without departing from the spirit of the scope of the present disclosure. For example, when an overall sanitizing, disinfecting, or cleaning process includes more than one method, measurements may be made to determine whether an appropriate level of cleanliness is reached after a first method is applied, and it may be determined that a second method is not necessary if the appropriate level of cleanliness has already been substantially achieved. Therefore, the present examples are to be considered as illustrative and not restrictive, and the examples are not to be limited to the details given herein, but may be modified within the scope of the appended claims.

What is claimed is:

1. A vehicle comprising:
a first compartment, the first compartment having a plurality of walls that define a space;
a first system, the first system configured to enable the vehicle to travel autonomously, the first system including a power system configured to provide power to the first compartment;
a second system, the second system configured to determine whether conditions around the vehicle are suitable for sanitization; and
a first sanitizing arrangement, the first sanitizing arrangement including at least a first sanitizing component, the at least first sanitizing component being included in the first compartment, wherein the first sanitizing arrangement is configured to be activated to sanitize the plurality of walls and the space when the vehicle determines that the first compartment is to be sanitized and when it is determined that the conditions around the vehicle are suitable for sanitization, the conditions around the vehicle being determined to be suitable for sanitization when the vehicle is in a physical location at which the vehicle may be safely sanitized, wherein the first sanitizing arrangement is a heating arrangement, and wherein the vehicle determines that the first compartment is to be sanitized when the conditions around the vehicle are determined to be suitable for sanitization and the first compartment does not contain at least one selected from a group including steam and condensation.

2. The vehicle of claim 1 further including:
a second sanitizing arrangement, the second sanitizing arrangement configured to provide ultraviolet (UV) sanitization to sanitize the plurality of walls and the space, wherein it is determined that the conditions around the vehicle are suitable for sanitization when there are no humans near the vehicle.

3. The vehicle of claim 1 further including:
an exterior surface;
a cleaning arrangement configured to clean the exterior surface.

4. The vehicle of claim 1 further including:
a sterilizing film, wherein the sterilizing film is coupled to at least one wall of the plurality of walls.

5. The vehicle of claim 1 wherein the plurality of walls is included in a compartment insert, the compartment insert configured to be carried in the first compartment and to obtain power from the first compartment.

6. A method comprising:
determining when a compartment onboard a vehicle is to be cleaned, the vehicle including at least a first cleaning arrangement, the first cleaning arrangement configured to implement a cleaning process to clean the compartment, wherein the first cleaning arrangement includes at least one ultraviolet (UV) light source;
determining at least one parameter for the cleaning process when it is determined that the compartment is to be cleaned;
determining whether the vehicle is in condition to be cleaned when it is determined that the compartment is to be cleaned, wherein determining whether the vehicle is in condition to be cleaned includes determining whether a door to the compartment is closed and at least one condition around the vehicle is suitable, wherein the vehicle is in the condition to be cleaned when the door to the compartment is closed and the at least one condition around the vehicle is suitable when the vehicle provides a prompt to move away from the vehicle;
activating the first cleaning arrangement to initiate the cleaning process when it is determined that the vehicle is in condition to be cleaned and the at least one condition around the vehicle is suitable, wherein activating the first cleaning arrangement includes activating the at least one UV light source, wherein activating the at least one UV light source causes the UV light source to generate a light wave with a wavelength in a range of approximately 200 nanometers (nm) to approximately 300 nm, and wherein determining whether the vehicle is in condition to be cleaned further includes determining whether there is at least one selected from a group including steam and condensation in the compartment, wherein when it is determined that there is the at least one of the steam and the condensation in the compartment, the vehicle is determined not to be in condition to be cleaned;
determining when the compartment is at a desired level of cleanliness after initiating the cleaning process;
continuing the cleaning process when it is determined that the compartment is not at the desired level of cleanliness; and
deactivating the first cleaning arrangement to end the cleaning process when it is determined that the compartment is at the desired level of cleanliness.

7. The method of claim 6 wherein the compartment contains an item to be delivered to a customer and the cleaning process causes the item to be cleaned, and wherein the at least one parameter is determined based on input provided by the customer.

\* \* \* \* \*